(12) United States Patent
Kelley et al.

(10) Patent No.: US 8,067,182 B2
(45) Date of Patent: Nov. 29, 2011

(54) METHOD OF WEAK PARTITIONING CHROMATOGRAPHY

(75) Inventors: Brian D. Kelley, Medford, MA (US); James E. Booth, Andover, MA (US); Paul Brown, Andover, MA (US); Jon Coffman, Hampstead, NH (US); Ranganathan Godavarti, Burlington, MA (US); Tim Iskra, Derry, NH (US); Shujun Sun, Brentwood, NH (US); Mary B. Switzer, North Andover, MA (US); Suresh Vunnum, Burlington, MA (US); Tianning Yu, Arlington, MA (US)

(73) Assignee: Wyeth LLC, Madison, NJ (US)

( * ) Notice: Subject to any disclaimer, the term of this patent is extended or adjusted under 35 U.S.C. 154(b) by 707 days.

(21) Appl. No.: 11/372,054

(22) Filed: Mar. 10, 2006

(65) Prior Publication Data

US 2007/0060741 A1 Mar. 15, 2007

Related U.S. Application Data

(60) Provisional application No. 60/660,437, filed on Mar. 11, 2005.

(51) Int. Cl.
*G01N 33/53* (2006.01)
*C07K 14/00* (2006.01)

(52) U.S. Cl. .................. 435/7.1; 436/514; 530/412

(58) Field of Classification Search .................. None
See application file for complete search history.

(56) References Cited

U.S. PATENT DOCUMENTS

| | | | | |
|---|---|---|---|---|
| 4,029,583 A | 6/1977 | Chang et al. ................ 210/502 |
| 4,983,722 A | 1/1991 | Bloom et al. |
| 5,429,746 A | 7/1995 | Shadle et al. |
| 5,451,662 A | 9/1995 | Naveh et al. |
| 5,644,036 A | 7/1997 | Ramage et al. |
| 6,177,548 B1 | 1/2001 | Wan et al. |
| 7,122,641 B2 | 10/2006 | Vedantham et al. ........ 530/413 |
| 2005/0107594 A1* | 5/2005 | Sun et al. ................ 530/387.1 |
| 2006/0194953 A1 | 8/2006 | Bonnerjea et al. ......... 530/387.1 |
| 2007/0054390 A1* | 3/2007 | Kelley et al. ................. 435/183 |

FOREIGN PATENT DOCUMENTS

| | | |
|---|---|---|
| WO | WO 95/22389 | 8/1995 |
| WO | WO-03/059935 | 7/2003 |
| WO | WO-2004/076485 | 9/2004 |
| WO | WO-2005/044856 | 5/2005 |

OTHER PUBLICATIONS

Fahrner and Blank, "Real-time monitoring of recombinant antibody breakthrough during Protein A affinity chromatography", Biotechnology and Applied Biochemistry 29 Pt. 2: 109-112 (1999).*
Gareil et al. "Study of non-linear elution in preparative liquid chromatography" (1980) *J. Chromatogr.* 192:53-74, (English abstract only).
International Search Report in PCT/US2006/08919 (Sep. 10, 2007).
International Preliminary Report on Patentability/Written Opinion in PCT/US2006/08919 (Sep. 25, 2007).
Search Report and Written Opinion in Singapore Application No. 0706165-8 (Nov. 20, 2008).
Kelley et al., "Weak Partitioning Chromatography for Anion Exchange Purification of Monoclonal Antibodies", Biotechnology and Bioengineering 101(3):553-566 (2008).

* cited by examiner

*Primary Examiner* — Anand Desai

(57) ABSTRACT

This invention relates to methods of using weak partitioning chromatography for the purification of a product from a load fluid containing one or more impurities. Further, the invention relates to methods of weak partitioning chromatography defined by operating conditions which cause a medium to bind least 1 mg of product per mL of medium, or alternatively, defined by a partition coefficient of at least 0.1.

44 Claims, 15 Drawing Sheets

A

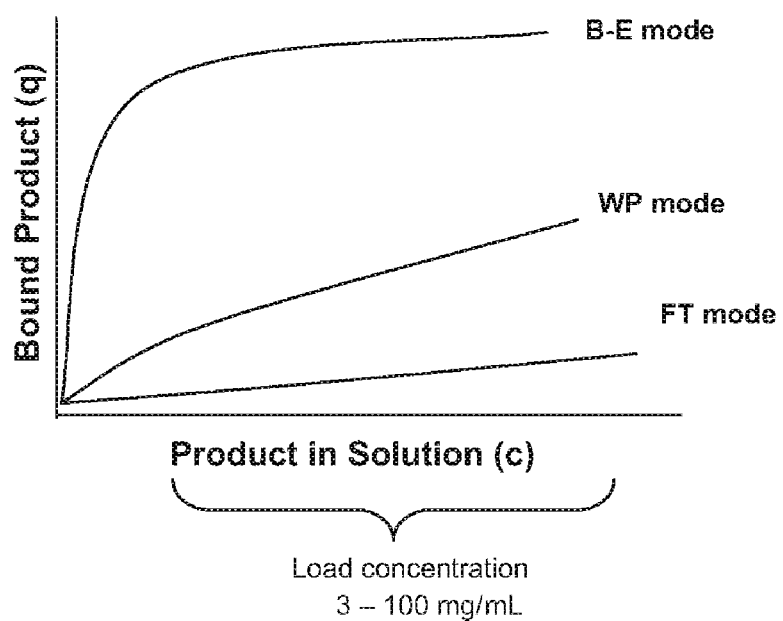

FIGURE 3

- Bind-Elute (B-E)
  - High $K_{Prod} > 20$
  - Capacity limit: product mass on resin (not load volume)
  - Change in mobile phase to elute product

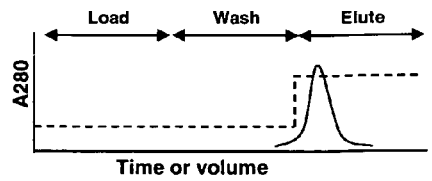

- Flowthrough (FT)
  - Very low $K_{Prod} < 0.1$
  - Capacity limit: impurity breakthrough and volume
  - Isocratic
  - Chromatogram with rapid breakthrough, washout

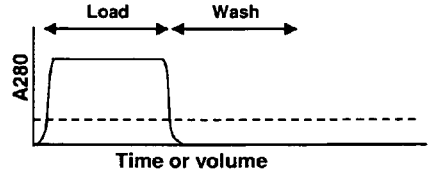

- Weak Partitioning (WP)
  - Intermediate $K_{Prod}$ $0.1 < K < 20$
  - Capacity improved over FT mode (both load volume & mass)
  - Isocratic
  - Delayed breakthrough, lagging washout

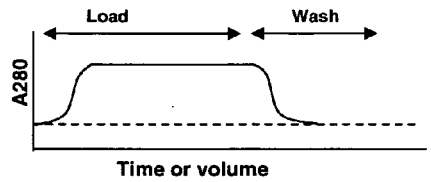

Figure 10
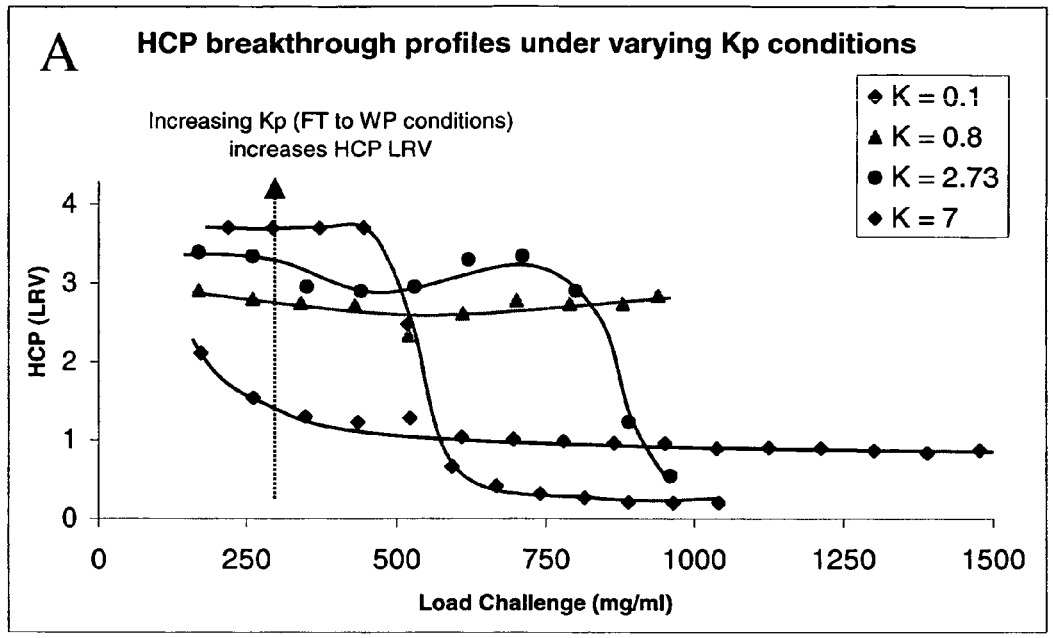
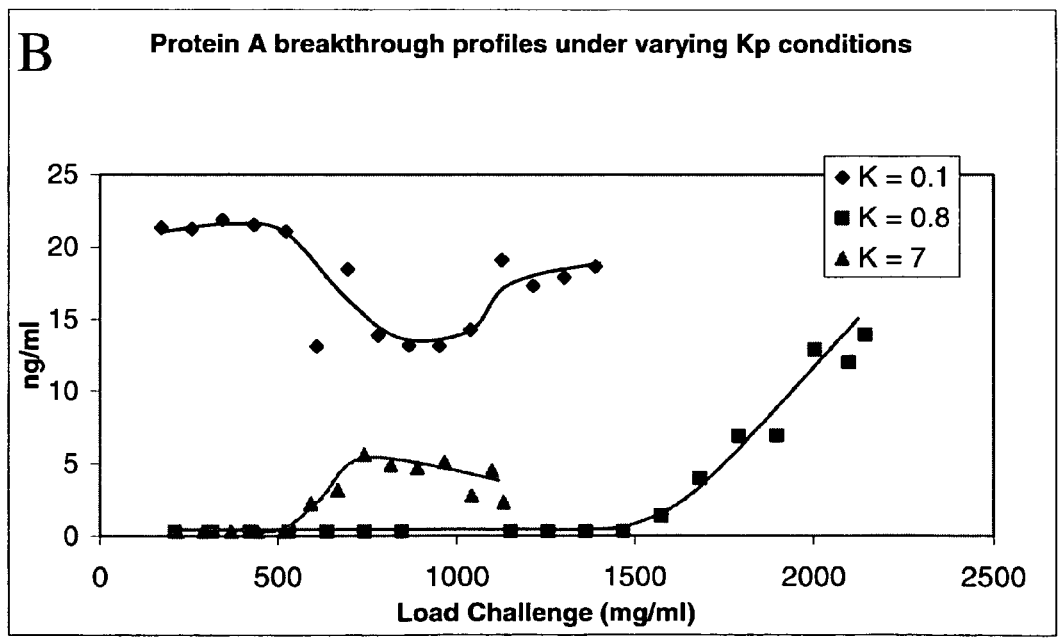

METHOD OF WEAK PARTITIONING CHROMATOGRAPHY

RELATED APPLICATIONS

This application claims the benefit under 35 U.S.C. §119(e) of U.S. Provisional Application No. 60/660,437, filed on Mar. 11, 2005, which is hereby incorporated by reference herein in its entirety.

FIELD OF THE INVENTION

The invention relates to methods of recovering a purified product from a load fluid including one or more impurities. In certain embodiments of the invention, the methods comprise passing the load fluid through a medium at operating conditions which cause the medium to bind at least 1 mg of product per mL of medium, and recovering the purified product in the column effluent during the load cycle and any essentially isocratic wash. In other embodiments of the invention, the methods comprise passing the load through a medium at operating conditions defined by a partition coefficient of at least 0.1.

BACKGROUND OF THE INVENTION

Within the biotechnology industry, the purification of proteins on a commercial scale is an important challenge to the development of recombinant proteins for therapeutic and diagnostic purposes. Problems related to yield, purity, and throughput plague the manufacturing sector. With the advent of recombinant protein technology, a protein of interest can be produced using cultured eukaryotic or prokaryotic host cell lines engineered to express a gene encoding the protein. What results from the host cell culturing process, however, is a mixture of the desired protein along with impurities that are either derived from the protein itself, such as protein variants, or from the host cell, such as host cell proteins. The use of the desired recombinant protein for pharmaceutical applications is contingent on being able to reliably recover adequate levels of the protein from these impurities.

Conventional protein purification methods are designed to separate the protein of interest from impurities based on differences in size, charge, solubility, and degree of hydrophobicity. Such methods include chromatographic methods such as affinity chromatography, ion exchange chromatography, size exclusion chromatography, hydrophobic interaction chromatography, immobilized metal affinity chromatography, and hydroxyapatite chromatography. These methods often employ a separation medium that can be designed to selectively adhere either the protein of interest or the impurities. In the bind-elute mode, the desired protein selectively binds to the separation medium and is differentially eluted from the medium by different solvents. In the flow-through mode, the impurities specifically bind to the separation medium while the protein of interest does not, thus allowing the recovery of the desired protein in the "flow-through."

Current methods for the purification of proteins, such as antibodies, include two or more chromatographic steps. For example, the first step in the protein purification protocol often involves an affinity chromatography step that utilizes a specific interaction between the protein of interest and an immobilized capture reagent. Protein A adsorbents are particularly useful for affinity capture of proteins, such as antibodies, which contain an Fc region. However, drawbacks to using Protein A chromatography for protein purification include leakage of the Protein A capture agent, leading to contamination of the eluted protein product. Additionally, affinity capture does not separate protein variants, such as aggregated forms of the protein, from the protein of interest.

Researchers have used bind-elute methods, flow-through methods, and displacement methods in efforts to recover proteins free from impurities resulting from both the culturing process and from possible prior steps in the purification process itself. Examples of groups using a bind-elute step as a typical second step to purifying proteins after an affinity capture step include: U.S. Pat. No. 4,983,722, describing a bind-elute ion exchange method of reducing Protein A from a mixture; U.S. Pat. No. 5,429,746, describing a bind-elute hydrophobic interaction chromatography method for purifying IgG antibody from a mixture including Protein A impurities; and U.S. Pat. No. 5,644,036, describing a three-step process for obtaining a purified IgG antibody preparation comprising a Protein A step, a bind-elute ion exchange step, and a size exclusion step. Other groups have used a flow-through step after the affinity chromatography step. For example, PCT publication WO 04/076485 describes a method for removing leaked Protein A from an antibody purified by a Protein A chromatography step followed by a flow-through ion exchange step. PCT publication WO 03/059935 describes a method for purifying a protein in a sample comprising subjecting the sample to a flow-through hydroxyapatite chromatography step following an affinity chromatography step.

Other groups have used a single polishing-step purification scheme to avoid the problems associated with prior purification steps. For instance, U.S. Pat. No. 6,177,548 describes a single-step flow-through ion exchange method for removing aggregates from a biological sample where the pH of the sample is adjusted to 0.2 logs below the isoelectric point of the biological sample. U.S. Pat. No. 5,451,662 describes a single-step bind-elute ion exchange method where the pH of the crude protein mixture is adjusted to a point between the ranges of isoelectric points of the protein fractions to be separated. PCT publication WO 05/044856 describes a single-step displacement method for removal of high molecular weight aggregates from antibody preparations using hydroxyapatite chromatography.

None of the conventional bind-elute or flow-through methods in the prior art, however, is able to meet the needs of the biotechnology industry in terms of all the requirements of throughput, yield, and product purity. Bind-elute methods and displacement methods are limited by, among other factors, the capacity limit of the separation medium for the desired protein. Flow-through methods, on the other hand, do allow for higher load challenges than bind-elute methods but are limited by the capacity of the separation medium for the impurities. With flow-through methods, no substantial binding of the product to the column occurs; any substantial product binding is seen as negatively impacting product recovery. There is still a need for methods of recovering purified proteins at high throughput that meet the requirements for purity and yield necessary for therapeutic and diagnostic applications. In addition, commercial manufacturing processes add the needs for reliable, robust, and cost-effective purification schemes.

SUMMARY OF THE INVENTION

The present invention relates to methods of recovering a purified product from a load fluid including one or more impurities by passing the load fluid through a medium at operating conditions which cause the medium to bind at least 1 mg of product per mL of medium and recovering the purified product in the column effluent during the load cycle and any essentially isocratic wash. In other embodiments, the operating conditions cause the medium to bind at least 5 mg of product per mL of medium. In another embodiment, the operating conditions cause the medium to bind at least 10 mg of product per mL of medium. In other embodiments, the operating conditions cause the medium to bind at least 20, 30, 40, 50, or 60 mg of product per mL of medium.

The present invention also relates to methods of recovering a purified product from a load fluid including one or more impurities by passing the load fluid through a medium at operating conditions defined by a partition coefficient of at least 0.1 and recovering the purified product in the column effluent during the load cycle and any essentially isocratic wash. In one embodiment, the partition coefficient is in the range of about 0.2 to about 20.0. In another embodiment, the partition coefficient is in the range of about 0.2 to about 10.0. In another embodiment, the partition coefficient is in the range of about 1.0 to about 5.0. In another embodiment, the partition coefficient is in the range of about 0.5 to about 5.0. In an additional embodiment, the partition coefficient is in the range of about 0.5 to about 1.5.

The present invention also relates to methods of recovering a purified product from a load fluid including one or more impurities by passing the load fluid through a medium at operating conditions which cause the medium to bind from at least 1 to about 70 mg of product per mL of medium and defined by a partition coefficient of 0.3 to 20, and recovering the purified product in the column effluent during the load cycle and any essentially isocratic wash.

The invention also provides for identifying, in a screening step, the operating conditions that cause the medium to bind at least 1 mg product per mL of medium or alternatively, are defined by a partition coefficient of at least 0.1. The screening step can employ batch binding studies or column binding studies, such as gradient elution studies or isocratic elution studies.

Operating conditions include pH levels, ionic strengths, salt concentrations, excipient concentrations (such as phosphate concentrations, calcium concentrations, arginine concentrations, glycine concentrations, and HEPES concentrations), and counterligand levels (such as imidazole concentrations), depending on the selection of medium.

The medium can be any type of chromatographic resin or separation medium, including a charged ion exchange medium, such as an anion exchange medium or a cation exchange medium, a hydrophobic interaction chromatography resin, a hydroxyapatite resin, or an immobilized metal affinity chromatography resin.

Purified products that can be recovered using the invention include fusion proteins, Fc-containing proteins, immunoconjugates, cytokines, interleukins, hormones, and therapeutic enzymes.

Impurities that can be removed using the invention include host cell proteins, nucleic acids, product variants, endotoxins, Protein A, and viruses.

In one embodiment, the medium removes at least 99.9% of the impurities in the load fluid including host cell proteins, nucleic acids, product variants, endotoxins, and Protein A.

In another embodiment, the concentration of product variants in the purified product is no more than about 2%.

In additional embodiments, the load onto the medium may be at a load challenge of at least 500 mg or at least 1000 mg of product per mL of medium.

In one aspect of the invention, a purified product is recovered from a load fluid including one or more impurities by passing the load fluid through a charged ion exchange medium at operating conditions comprising pH levels and ionic strengths which cause the medium to bind at least 1 mg of product per mL of medium or alternatively, at operating conditions defined by a partition coefficient of at least 0.1.

In another aspect of the invention, a purified product is recovered from a load fluid including one or more impurities by passing the load fluid through a hydrophobic interaction chromatography resin at operating conditions comprising pH levels, ionic strengths, and salt concentrations which cause the medium to bind at least 1 mg of product per mL of medium or alternatively, at operating conditions defined by a partition coefficient of at least 0.1.

In another aspect of the invention, a purified product is recovered from a load fluid including one or more impurities by passing the load fluid through a hydroxyapatite chromatography resin at operating conditions comprising pH levels, ionic strengths, phosphate concentrations, calcium concentrations, arginine concentrations, glycine concentrations, HEPES concentrations, and imidazole concentrations which cause the medium to bind at least 1 mg of product per mL of medium or alternatively, at operating conditions defined by a partition coefficient of at least 0.1.

In yet another aspect of the invention, a purified product is recovered from a load fluid including one or more impurities by passing the load fluid through an immobilized metal affinity chromatography resin at operating conditions comprising counterligand levels and pH levels which cause the medium to bind at least 1 mg of product per mL of medium or alternatively, at operating conditions defined by a partition coefficient of at least 0.1.

The methods of the invention can be optionally combined with one or more purification steps. The optional step(s) can be performed either prior to or following the practice of the inventive method. For example, the methods of the invention can optionally be combined with a Protein A chromatography step as an initial step.

In one embodiment of the invention, a product-containing fluid is eluted from a Protein A column using an elution buffer of low ionic strength; the pH and conductivity of the product-containing fluid is adjusted using a neutralization buffer which results in no more than 20 mM of the ionic strength of the product-containing fluid, resulting in the load fluid; and the load fluid is passed through an anion exchange medium under the operating conditions of the invention.

In some embodiments, the elution buffer comprises molecules with a charged cationic group with a pKa of 6.5-10. In other embodiments, the elution buffer further comprises molecules with a charged anionic group with a pKa of 2-5. In certain embodiments, the elution buffer comprises molecules which are zwitterions at pHs between 7 and 9.

The invention also provides for purified products, including purified proteins and antibodies, prepared by the methods of the invention.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute part of this specification, and together with the description, serve to explain the principles of the invention.

BRIEF DESCRIPTION OF THE FIGURES

FIG. 3 shows schematic chromatograms for three modes of operation: bind-elute mode, weak partitioning mode, and flow-through mode.

FIG. 10 shows (A) for Mab-AAB, host cell protein breakthrough profiles as a function of Kp in ion exchange chromatography; and (B) for Mab-AAB, Protein A breakthrough as a function of Kp in ion exchange chromatography.

DETAILED DESCRIPTION OF THE INVENTION

A. Definitions

In order that the present invention may be more readily understood, certain terms are first defined. Additional definitions are set forth throughout the detailed description.

The term "flow-through mode" refers to a product preparation separation technique in which at least one product contained in the preparation is intended to flow through a chromatographic resin or medium, while at least one potential contaminant or impurity binds to the chromatographic resin or medium. Generally, the product partition coefficient for flow-through mode is less than 0.1 and bound product concentration is <1 mg/mL. The "flow-through mode" is an isocratic operation.

The term "bind-elute mode" refers to a product preparation separation technique in which at least one product contained in the preparation binds to a chromatographic resin or medium. Generally, the product partition coefficient for bind-elute mode is greater than 20 and the bound product concentrations are between 1-20 mg/mL. The bound product in this mode is eluted during the elution phase.

The term "weak partitioning mode" refers to a product preparation separation technique in which at least one product contained in the preparation, and at least one contaminant or impurity, both bind to a chromatographic resin or medium. The binding of product in weak partitioning mode is at least 1 mg of product per mL of chromatographic resin or medium. Generally, the product partition coefficient for weak partitioning mode is at least 0.1. The "weak partitioning mode" is an isocratic operation.

Figure 1:
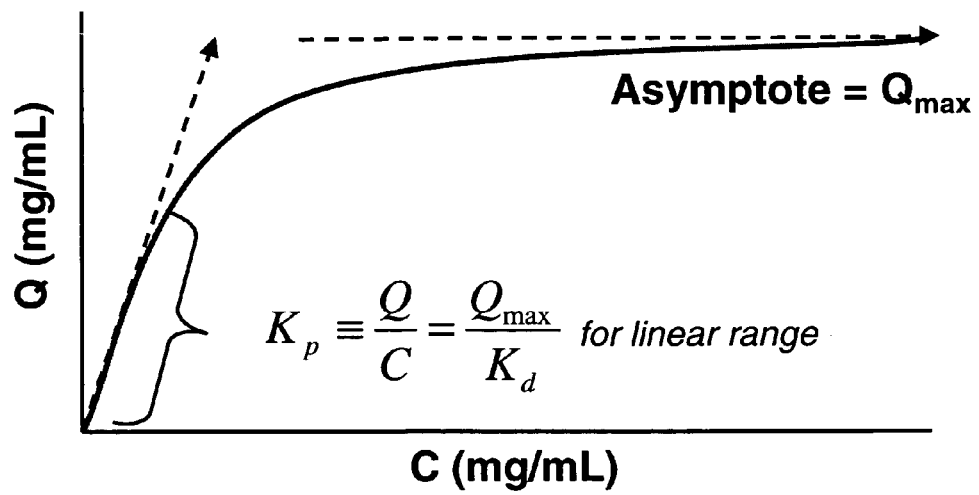
FIG. 1 shows (A) the relationship between a partition coefficient and a product adsorption isotherm; and (B) adsorption isotherms for product binding to resin, for three modes of operation: bind-elute mode, weak partitioning mode, and flow-through mode.

The term "partition coefficient" (Kp) refers to the equilibrium ratio of the concentration of product absorbed to the resin (O) to the concentration of product in the solution (c), under specified conditions of pH and solution composition. The partition coefficient Kp is also related to the product adsorption isotherms as shown in FIG. 1. The partition coefficient Kp corresponds to the slope of the product adsorption isotherm at very low solution concentrations. It is related to the maximum capacity as follows:

$$K_P = \frac{Q}{C} = \frac{Q_{max}}{k_d}$$

where $Q_{max}$ is to maximum capacity of the resin for the product, and $k_d$ is the dissociation constant for 'resin—product' interaction. The partition coefficient is typically measured with a batch binding technique, but other techniques, such as isocratic chromatography, can be used.

The term "bound product" (O) refers to the amount of product which binds to the resin when in equilibrium with a feedstream.

The term "antibody" refers to any immunoglobulin or fragment thereof, and encompasses any polypeptide comprising an antigen-binding site. The term includes, but is not limited to, polyclonal, monoclonal, monospecific, polyspecific, non-specific, humanized, human, single-chain, chimeric, synthetic, recombinant, hybrid, mutated, grafted, and in vitro generated antibodies. The term "antibody" also includes antibody fragments such as Fab, F(ab')$_2$, Fv, scFv, Fd, dAb, and other antibody fragments that retain antigen-binding function. Typically, such fragments would comprise an antigen-binding domain.

In certain embodiments of the invention, the antibody is one which comprises a $C_H2/C_H3$ region and therefore is amenable to purification by Protein A chromatography. The term "$C_H2/C_H3$ region" refers to those amino acid residues in the Fc region of an immunoglobulin molecule which interact with Protein A. In some embodiments, the $C_H2/C_H3$ region comprises an intact $C_H2$ region followed by an intact $C_H3$ region, and in other embodiments, comprises a Fc region of an immunoglobulin. Examples of $C_H2/C_H$ region-containing proteins include antibodies, immunoadhesions and fusion proteins comprising a protein of interest fused to, or conjugated with, a $C_H2/C_H3$ region.

The term "load" refers to any load material containing the product, either derived from clarified cell culture or fermentation conditioned medium, or a partially purified intermediate derived from a chromatography step. The term "load fluid" refers to a liquid containing the load material, for passing through a medium under the operating conditions of the invention.

The term "impurity" refers to any foreign or objectionable molecule, including a biological macromolecule such as a DNA, an RNA, or a protein, other than the protein of interest being purified that is also present in a sample of the protein of interest being purified. Impurities include, for example, protein variants, such as aggregated proteins, high molecular weight species, low molecular weight species and fragments, and deamidated species; other proteins from host cells that secrete the protein being purified (host cell proteins); proteins that are part of an absorbent used for affinity chromatography that may leach into a sample during prior purification steps, such as Protein A; endotoxins; and viruses.

The term "essentially isocratic wash" refers to a solution which varies only slightly from the load fluid in terms of composition or pH.

The term "column effluent" refers to the liquid exiting the medium or column during the load cycle, or in the period that the load is being applied.

The term "load challenge" refers to the total mass of product loaded onto the column in the load cycle of a chromatography step or applied to the resin in batch binding, measured in units of mass of product per unit volume of resin.

The term "log removal value" (LRV) refers to the log(base 10) of the ratio of the mass of impurity in the load of a purification step to the mass of impurity in the product pool.

The term "isocratic chromatography" refers to the operation of a chromatographic column with a solvent that does not change strength during the period of interest.

B. Description of the Method

The present invention provides methods for recovering purified products from a load fluid containing one or more impurities. The invention has application to the large-scale preparation of proteins for therapeutic and diagnostic purposes.

1. Weak Partitioning Mode

Applicants have surprisingly found that by operating in a chromatographic mode residing in the region between conventional bind-elute and flow-through chromatography modes, a high degree of impurity reduction, as well as high product load challenge and product recovery, can be obtained. Applicants have named this intermediate product binding mode, the "weak partitioning mode."

In weak partitioning mode, a load fluid containing a product of interest and one or more impurities is passed through a chromatographic medium, with both the product and the impurities binding to the medium. However, the impurities bind more tightly to the medium than the product and as loading continues, unbound product passes through the medium and is recovered from the column effluent. The medium is optionally subsequently washed under isocratic conditions to recover additional weakly bound product from the medium and the purified product from any essentially isocratic wash is pooled with the purified product from the column effluent during the load cycle.

In accordance with the invention, weak partitioning mode is defined by operating conditions which cause the medium to bind at least 1 mg of product per mL of medium. In one embodiment, the operating conditions cause the medium to bind at least 5 mg of product per mL of medium. In another embodiment, the operating conditions cause the medium to bind at least 10 mg of product per mL of medium. In another embodiment, the operating conditions cause the medium to bind at least 20, 30, 40, 50, or 60 mg of product per mL of medium.

In certain embodiments of the invention, the total product mass bound to the medium is at least 10% of the total product mass loaded onto the medium. In some embodiments, the total product mass bound to the medium is at least 20% of the total product mass loaded onto the medium. In other embodiments, the total product mass bound to the medium is at least 30% of the total product mass loaded onto the medium.

In accordance with the invention, weak partitioning mode is also defined by a partition coefficient of at least 0.1. In some embodiments, operating in weak partitioning mode comprises operating under conditions defined by a partition coefficient in the range of about 0.2 to about 20.0. In certain embodiments, operating in weak partitioning mode comprises operating under conditions defined by a partition coefficient in the range of about 0.2 to about 10.0. In other embodiments, operating in weak partitioning mode comprises operating under conditions defined by a partition coefficient in the range of about 1.0 to about 5.0. In other embodiments, operating in weak partitioning mode comprises operating under conditions defined by a partition coefficient in the range of about 0.5 to about 5.0. In yet other embodiments, operating in weak partitioning mode comprises operating under conditions defined by a partition coefficient in the range of about 0.5 to about 1.5.

At least one embodiment of the present invention provides weak partitioning mode operating conditions which cause the medium to bind from at least 1 to about 70 mg of product per mL of medium, and which are defined by a partition coefficient of 0.3 to 20.

FIG. 1 shows the product adsorption isotherms for the bind-elute, flow-through, and weak partitioning modes, with product binding for weak partitioning mode being clearly intermediate in comparison to bind-elute and flow-through modes. Because the value of the product partition coefficient (Kp) is the ratio of the concentration of the adsorbed product to the concentration of the product in solution, the Kp values for weak partitioning mode are also intermediate to the values for bind-elute and flow-through modes.

Figure 2:
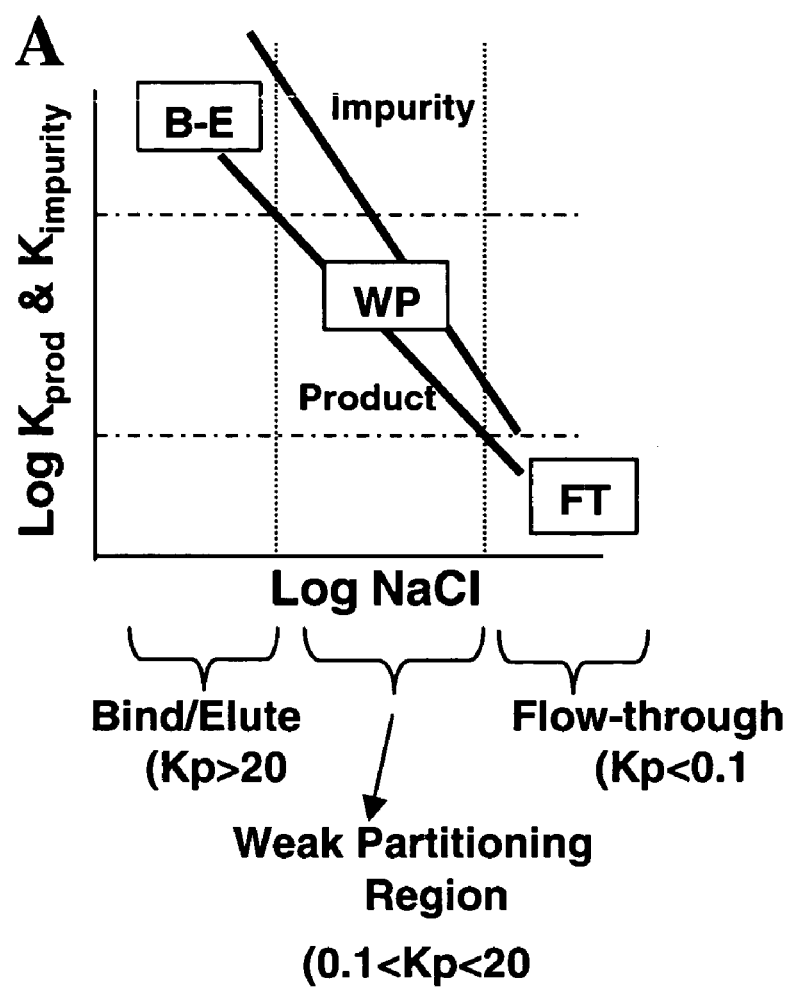
FIG. 2 shows (A) the partitioning regions for three modes of operation in ion exchange chromatography: bind-elute mode, weak partitioning mode, and flow-through mode; and (B) the partitioning regions for three modes of operation in hydroxyapatite.
Figure 2B:
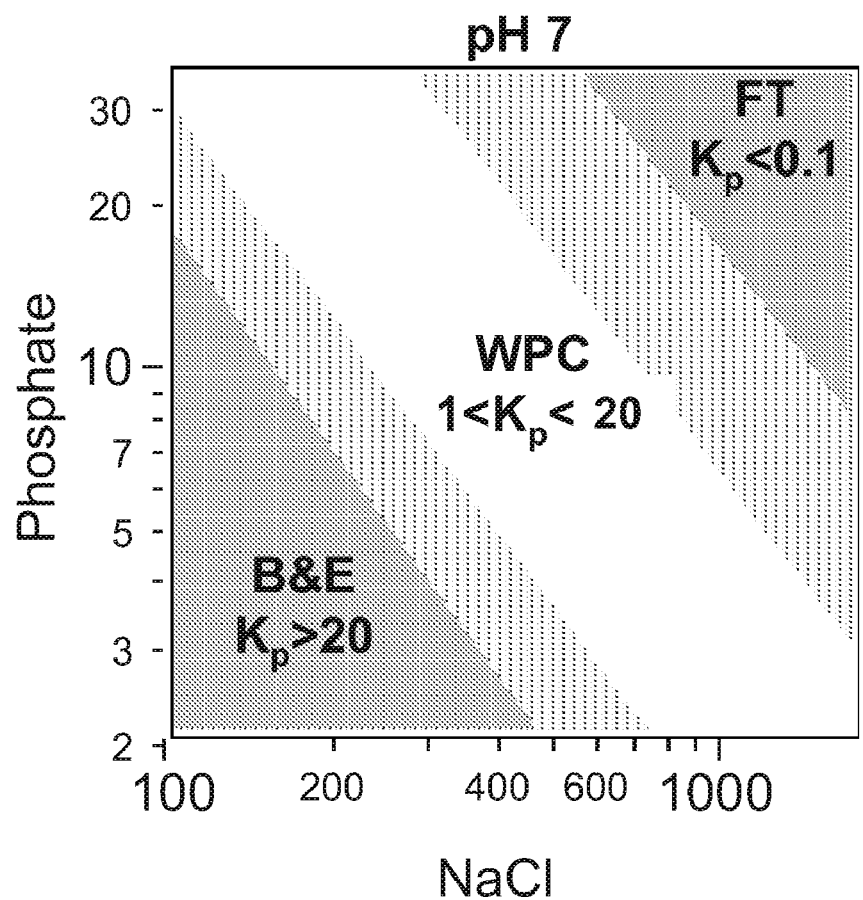

FIG. 2A depicts the partitioning regions for bind-elute, weak partitioning, and flow-through modes as a function of ionic strength, showing that $K_{imp}$ is higher in weak partitioning mode than in flow-through mode. Under the more stringent binding conditions of weak partitioning mode, a higher product capacity can be achieved—higher than flow-through mode, as impurities are more strongly bound, and higher than bind-elute mode, as the product binds very weakly in comparison to impurities and does not take up the majority of the resin capacity. The impurity partition coefficient ($K_{imp}$) is higher at more stringent binding conditions, resulting in lower concentrations of residual impurities in the product pool of weak partitioning mode compared to the product pool of flow-through mode. The flow-through, weak partitioning and bind-elute regions in hydroxyapatite, as a function of phosphate and NaCl concentration, are shown in FIG. 2B.

Table A summarizes the differences in characteristics between the three modes of binding: bind-elute (B-E), weak partitioning (WP), and flow-through (FT).

TABLE A

Characteristics of FT/WP/B-E modes

| | FT | WP | B-E |
|---|---|---|---|
| Kp | <0.1 | 0.1-20 | >20 |
| Load challenge limitation | Impurities 10-50 mg Prod/mL (typical) but actually dependent on load purity | Impurities 50-500 mg Prod/mL (typical) but actually dependent on load purity | Product + impurities <100 mg Prod/mL |
| Load Vol | Moderate, for dilute impurities 10-20 CVs | Very high, for dilute impurities up to 50 CVs | Lower, as the product binds in addition to impurities 5-20 CVs |
| [Product] in load eluate | Equal to load concentration through much of load | Initial lag, then equal to load concentration through much of load | <5% of load concentration |
| Residual [Impurity] | Low | Very low | Dependent on elution conditions, pool volume and capacity. |
| Product bound (Q) | <1 mg/mL | <10-20 mg/mL | >10-20 mg/mL |
| Operating region | Relatively broad range of conditions | Modest window of operation between FT and B-E modes | Stringent binding conditions for load, broad range of elution conditions |
| Mobile phase(s) | Isocratic | Isocratic | Change in buffer composition after load which causes elution. |

Figure 4:
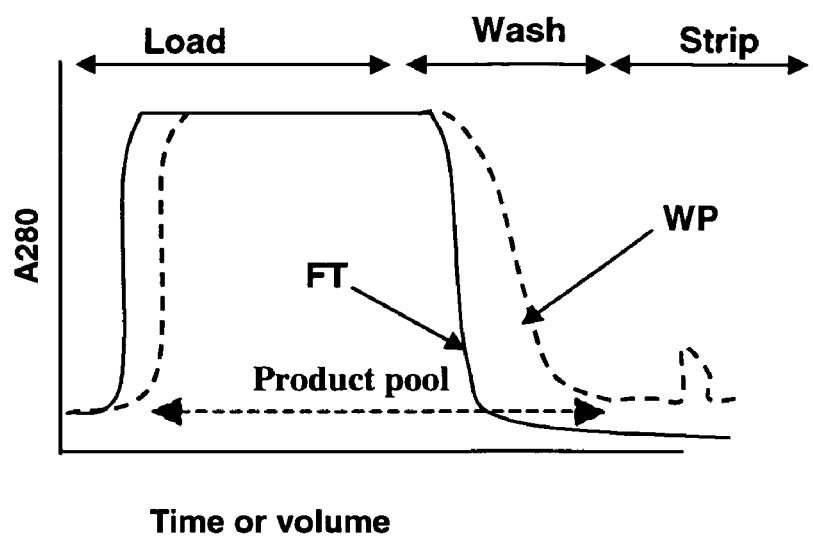
FIG. 4 shows a comparison between weak partitioning and flow-through chromatograms.

Weak partitioning mode can also be distinguished from bind-elute and flow-through modes by their chromatograms, as shown in FIG. 3. At first, the chromatograms for flow-through and weak partitioning modes may seem quite similar—the product is recovered in the column effluent and wash fractions, under isocratic conditions. However, subtle, but meaningful distinctions exist in the chromatograms which can be used to distinguish these modes, as shown in FIG. 4. There is a delay in the initial breakthrough profile (>0.1 column volumes or CV) for weak partitioning mode compared to flow-through mode. There is a slower washout profile in weak partitioning mode. A small strip peak containing product may be present (which corresponds to the resin still binding 10-50% of the load product concentration after the wash stage), which can be recovered from the resin by applying a 1-5 CV wash after the load under isocratic conditions subsequent to recovery of the column effluent during the load cycle.

Figure 5:
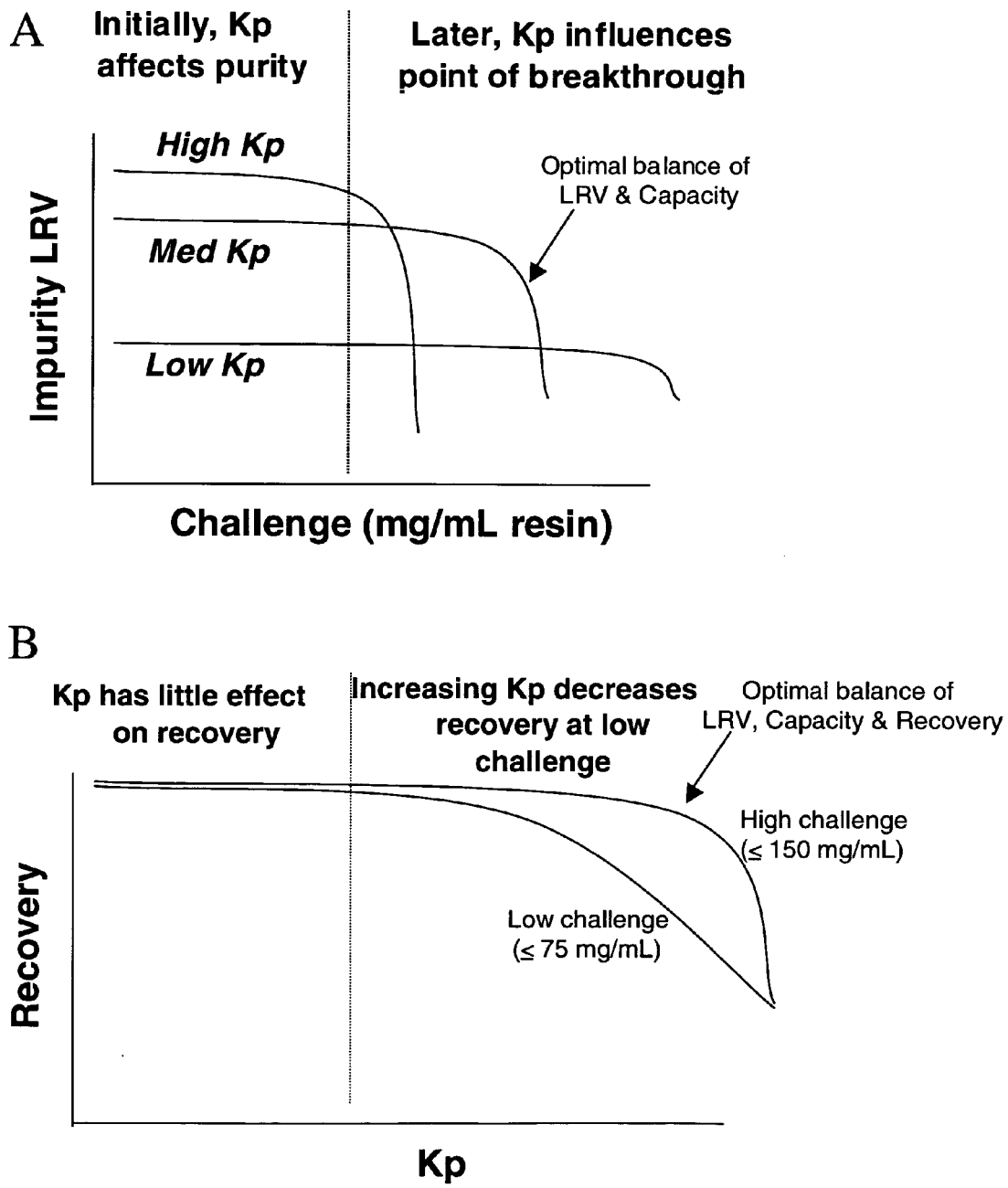
FIG. 5 shows (A) typical contaminant removal profiles as a function of Kp; and (B) recovery as a function of load challenge and Kp.

FIG. 5A shows the general trends in contaminant LRV for various levels of product partition coefficient values. Contaminant LRVs are relatively low at Kp conditions corresponding to flow-through operations. Operating under conditions of increasing Kp significantly increases LRVs in the column effluent fractions prior to contaminant breakthrough. As shown in the examples, operating at higher Kp values improves the contaminant LRVs by as much as 2 logs from those corresponding to the standard flow-through conditions.

Increasing Kp typically increases both the product as well as contaminant binding to the resin. The stronger binding of the contaminant at higher Kp leads to a greater LRV in the column effluent fractions prior to contaminant breakthrough. However, the load challenge at the point of contaminant breakthrough decreases with increasing Kp as the product begins to compete with the contaminant for the binding sites on the resin, as schematically represented in FIG. 5A by the high Kp curve. The weak partitioning region therefore corresponds to an operating window that balances the improvement in contaminant LRV with column capacity requirements for a given separation.

The upper Kp limit for weak partitioning chromatography is also dependent on the column load challenge as shown in FIG. 5B. The partition coefficient has no impact on product recovery at values bordering flow-through conditions. The product recovery begins to drop at high Kp values where the isocratic wash conditions are is not effective at washing the bound product off the column in a reasonable number of wash volumes. The extent of product loss due to ineffective washout is sensitive to load challenge, as well as the nature and proportion of contaminant in the load. Thus, the lower limit of the WP region is defined by requirements of contaminant removal, while the upper limit for a given load challenge is defined by constraints of product recovery or capacity.

Figure 6:
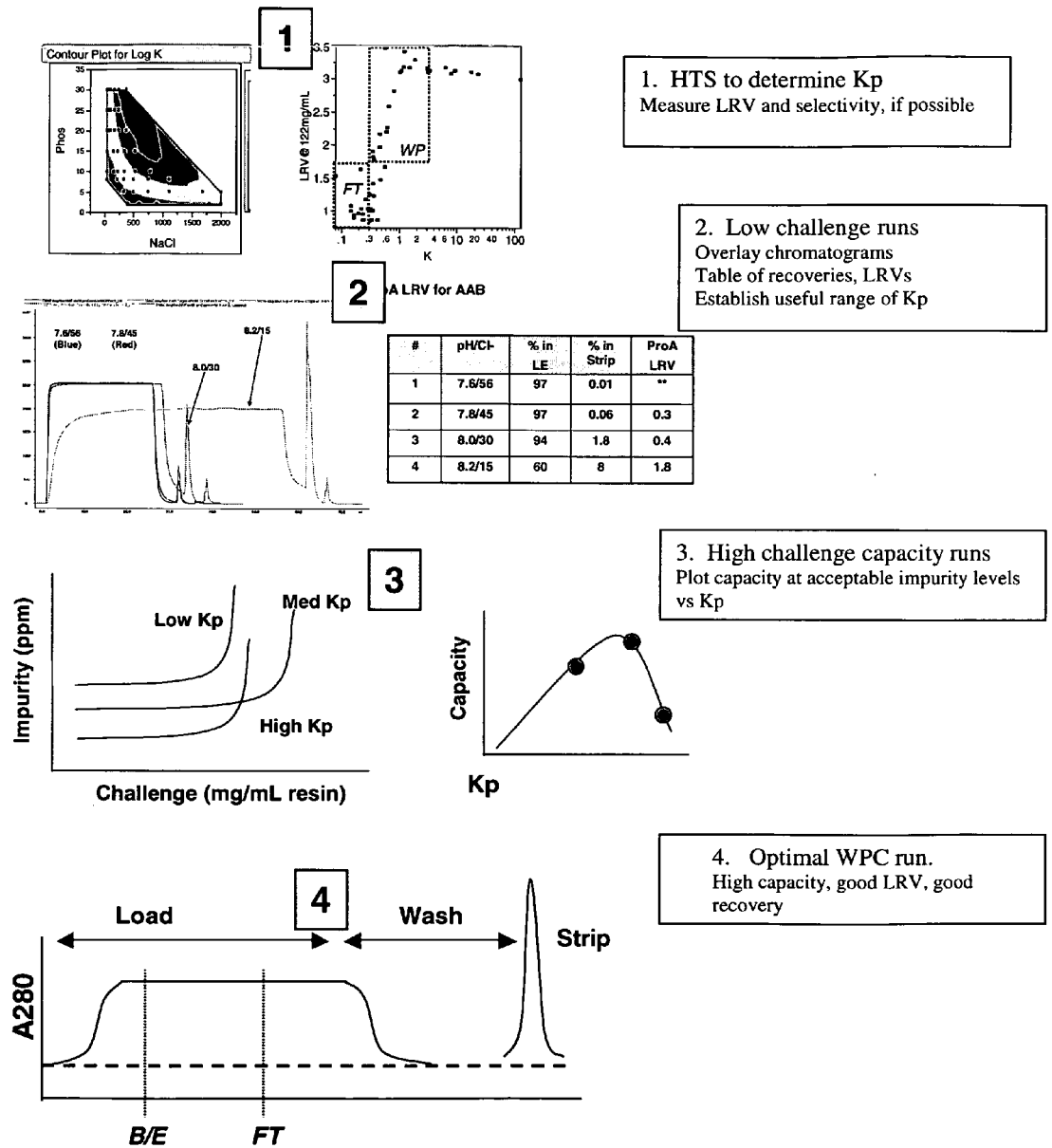
FIG. 6 shows typical progression of weak partitioning chromatography step development, including 1) high throughput screen to determine Kp, 2) low load challenge runs, 3) high challenge capacity runs, and 4) optimal weak partitioning runs.

In one or more embodiments of the invention, optimal weak partitioning conditions may be identified using the following sequence of experiments, as shown in FIG. 6:

(i) Perform a HTS screen (or standard batch binding experiments) to determine product partition coefficients $K_p$ as a function of operating conditions. Identify operating window corresponding to the weak partitioning region (0.1<Kp<20) from these experiments.

(ii) Preferably, after identifying the weak partitioning region, one can perform scouting runs on a small scale column at a load challenge similar to those used for standard flow-through operation (approximately 50 mg/mL). One can further fine-tune the weak partitioning operating window based on contaminant removal and product recovery values from these experiments.

(iii) More preferably, one can then generate contaminant breakthrough data for a few Kp conditions within the weak partitioning region. Based on these results, select an optimum partition coefficient in the weak partitioning region that provides the highest removal of contaminants at an acceptable load challenge.

(iv) One can then most preferably perform weak partitioning chromatography runs under optimal $K_p$ conditions and further fine-tune the load challenge and wash volumes as needed to obtain optimal recovery and contaminant removal.

One of skill in the art could use these guidelines or a variation thereof to easily define a weak partitioning chromatography step that provides enhanced contaminant removal at comparable or higher load challenges than standard flow-through or bind/elute modes of column operation. The general framework discussed above can, with minor adjustments if any, be applied to develop a purification step in an ion exchange, hydrophobic interaction, hydroxyapatite, or multimode system that combines elements of any or all of these interactions.

2. Separation Techniques

Weak partitioning mode may be used in conjunction with any chromatographic resin or medium for separation of a product from impurities. In one embodiment, the medium is a charged ion exchange medium. Ion exchange is a form of chromatography that separates according to net charge. Separation of molecules occurs as a result of the competition between the charged product of interest and counterions for oppositely charged ligand groups on the ion exchange medium. Binding interactions between the product and an ion exchange medium depend on the net charge of the product. Net charge is dependent on the pH and ionic strength of the medium, which affects the different charge characteristics of amino acids and other components on the exposed surface of the product molecule(s) of interest.

Ion exchange resins that may be used in the invention include anion exchange resins and cation exchange resins. Anionic exchange resins may employ substituents such as diethylaminoethyl (DEAE), trimethylaminoethyl (TMAE), quaternary aminoethyl (QAE) and quaternary amine (O) groups. Cationic exchange may employ substituents such as carboxymethyl (CM), sulfoethyl (SE), sulfopropyl (SP), phosphate (P) and sulfonate (S). Cellulosic ion exchange resins such as DE23, DE32, DE52, CM-23, CM-32 and CM-52 are available from Whatman Ltd. Maidstone, Kent, U.K. Sephadex-based and cross-linked ion exchangers are also known. For example, DEAE-, QAE-, CM-, and SP-Sephadex, and DEAE-, Q-, CM- and S-Sepharose, and Sepharose are all available from Amersham Biosciences, Piscataway, N.J. Further, both DEAE and CM derivatized ethylene glycol-methacrylate copolymer such as TOYOPEARL™ DEAE-650S or M and TOYOPEARL™ CM-650S or M are available from Toso Haas Co., Philadelphia, Pa.

In certain embodiments of the invention, weak partitioning mode is used with a hydrophobic interaction chromatography (HIC) resin for product purification. HIC is a technique for separating molecules based on hydrophobicity. Generally, sample molecules in a high salt buffer are loaded onto the HIC resin. The salt in the buffer interacts with water molecules to reduce the solution of the molecules in solution, thereby exposing hydrophobic regions in the sample molecules which are consequently absorbed by the HIC medium. The more hydrophobic the molecule, the less salt needed to promote binding. Binding interactions between the product molecules and a HIC medium thus depend on conditions such as pH, ionic strength, and salt concentrations of the medium.

Various commercially available HIC resins that can be used in the invention include resins comprising a base matrix (e.g., cross-linked agarose or synthetic copolymer material) to which hydrophobic ligands (e.g., alkyl or aryl groups) are coupled. Examples include Phenyl SEPHAROSE™ 6 FAST FLOW™ (Pharmacia LKB Biotechnology, AB, Sweden); Phenyl SEPHAROSE™ High Performance (Pharmacia LKB Biotechnology, AB, Sweden); Octyl SEPHAROSE™ High Performance (Pharmacia LKB Biotechnology, AB, Sweden); Fractogel™ EMD Propyl or FRACTOGEL™ EMD Phenyl (E. Merck, Germany); MACRO-PREP™ Methyl or MACRO-PREP™ t-Butyl Supports (Bio-Rad, CA); WP HI-Propyl ($C_3$)™ (J. T. Baker, N.J.); and TOYOPEARL™ ether, phenyl or butyl (TosoHaas, Pa.).

In other embodiments of the invention, weak partitioning mode is used with hydroxyapatite chromatography for product purification. Hydroxyapatite chromatography is a technique that utilizes an insoluble hydroxylated calcium phosphate of the formula $[Ca_{10}(PO_4)_6(OH)_2]$, as both the matrix and the ligand. Functional groups consist of pairs of positively charged calcium ions (C-sites) and clusters of negatively charged phosphate groups (P-sites). Binding interactions between the product and the hydroxyapatite medium depend on conditions such as the pH, ionic strength, and excipient concentrations, such as phosphate concentrations, calcium concentrations, arginine concentrations, glycine concentrations, and HEPES concentrations of the medium. Various hydroxyapatite chromatographic resins are available commercially and can be used in the invention.

In further embodiments of the invention, weak partitioning mode is used with an immobilized metal affinity chromatography (IMAC) resin for product purification. IMAC is based on the interaction between chelated transition metal ions immobilized on the resin and the imidazole side chains of histidine residues on the tagged product of interest. Separation of molecules occurs as a result of competition between the tagged product of interest and counterligands for metal groups on the IMAC resin. Binding interactions between the product and metal-charged IMAC medium depend on conditions such as counterligand levels, such as imidazole concentrations, and ionic strength of the medium. Various IMAC resins are available commercially and can be used in the invention.

3. Products for Purification

The invention can be used for the commercial-scale purification of various products of interest, including naturally occurring proteins, fusion proteins, Fc-containing proteins, immunoconjugates, cytokines, interleukins, hormones, and therapeutic enzymes. In one embodiment, the protein undergoing purification may comprise one or more constant antibody immunoglobulin domain(s). In one embodiment, the protein may also comprise a single or multiple variable antibody immunoglobulin domain(s). In another embodiment, the Fc-containing protein may comprise an antibody. The proteins can be derived from various sources, including cultured recombinant prokaryotic or eukaryotic host cell lines.

The antibody preparations of the invention can be isolated from a number of sources including, but not limited to, serum of immunized animals, ascites fluid, hybridoma or myeloma supernatants, conditioned media derived from culturing a recombinant cell line that expresses the antibody molecule and from all cell extracts of antibody-producing cells. In one embodiment of the invention, antibodies from conditioned cell culture media of a variety of antibody producing recombinant cell lines are purified. Although one may expect some variation from cell line to cell line and among the various antibody products, based on the disclosure herein, it is well within the purview of one of ordinary skill in this art to adapt the invention herein to a particular combination of antibody protein and producing cell line.

For purposes of illustration only, this invention was applied to the purification of several antibodies of the IgG isotype. More specifically, this invention was applied to purification of a humanized, anti-A beta monoclonal antibody, an anti-GDF8 antibody, and a humanized, anti-IL-13 monoclonal antibody.

4. Loading Conditions and Capacities

Before loading the fluid containing the product and impurities onto the medium, it may be necessary to identify the region of weak partitioning by finding the operating conditions which cause the medium to bind at least 1 mg of product per mL of medium. In one embodiment, the operating conditions found cause the medium to bind at least 5 mg of product per mL of medium. In another embodiment, the operating conditions found cause the medium to bind at least 10 mg of product per mL of medium. In other embodiments, the operating conditions found cause the medium to bind at least 20 mg of product per mL of medium. Alternatively, the weak partitioning region is identified by finding the operating conditions defined by a partition coefficient of at least 0.1. In certain embodiments, the operating conditions found are defined by a partition coefficient in the range of about 0.2 to about 20.0. In other embodiments, the operating conditions found are defined by a partition coefficient in the range of about 0.2 to about 10.0. In yet other embodiments, the operating conditions found are defined by a partition coefficient in the range of about 1.0 to about 5.0, in the range of about 0.5 to about 5.0, or in the range of about 0.5 to about 1.5. In additional embodiments, the weak partitioning region is identified by finding the operating conditions which cause the medium to bind from at least 1 to about 70 mg of product per mL of medium and which is defined by a partition coefficient of 0.3 to 20.

One skilled in the art will recognize that the appropriate operating conditions will depend on the choice of medium selected for purification of the product. In certain embodiments, the operating conditions comprise pH levels and ionic strengths. In other embodiments, the operating conditions further comprise salt concentrations. In yet other embodiments, the operating conditions further comprise excipient levels, such as phosphate concentrations and calcium concentrations. In some embodiments, the operating conditions comprise counterligand levels, such as imidazole concentrations, and pH levels.

A screening step can be used to identify the operating conditions for weak partitioning mode. Such a screening step could include batch binding studies or column binding studies. Column binding studies could include gradient elution studies or isocratic elution studies. For example, one skilled in the art can determine which buffer or salt is appropriate for the particular protein being purified and for the operating conditions that are being identified. The optimal concentration of the selected buffer or salt can then be determined by, for example, running a gradient of the selected buffer or salt through a column to which a load fluid comprising the product to be purified and the impurities has been applied. Fractions of the effluent of the column can be collected and analyzed to determine the concentration of buffer or salt at which product binding is at least 1 mg of product per mL of medium or alternatively, at which the partition coefficient for the product is at least 0.1. In certain embodiments of the invention, the partition coefficient is measured between 1 and 10 mg/mL load challenge with a phase ratio (volume of liquid to volume of resin) of three to six in a batch binding experiment.

Once the operating conditions are determined, the conditions of the load fluid and/or medium can be adjusted accordingly. For example, the medium can be equilibrated by washing it with a solution that will bring it to the necessary operating conditions of weak partitioning mode. The load fluid may also be buffer exchanged into an appropriate buffer or load buffer in preparation for weak partitioning mode. The load buffer can be the same or a different buffer as the equilibration buffer.

In one embodiment, the ionic strength of the load fluid is no more than 100 mM. In another embodiment, the ionic strength of the load fluid is no more than 50 mM. In another embodiment, the ionic strength of the load fluid is no more than 25 mM. In yet another embodiment, the ionic strength of the load fluid is no more than 10 mM.

The load fluid may be passed through a separation medium that is packed in a bed column, packed in a fluidized/expanded bed column containing the solid phase matrix, and/or in a batch format where the solid phase matrix is mixed with the load fluid for a certain time. After the load fluid is passed through the medium, the medium is optionally washed with a volume of essentially isocratic wash. Purified product can be obtained from any essentially isocratic wash and pooled with the purified product from the column effluent during the load cycle. After the optional wash step, the medium can optionally be stripped and regenerated. This procedure is typically performed regularly to minimize the buildup of impurities on the surface of the solid phase and/or to sterilize the medium to avoid contamination of the product with microorganisms.

High load concentrations and load volumes are possible with weak partitioning mode. In one embodiment, the concentration of product in the load fluid is at least 1 mg of product per mL of load fluid, in another embodiment, the concentration of product in the load fluid is at least 5 mg of product per mL of load fluid, in another embodiment, at least 50 mg of product per mL of load fluid, and in another embodiment, at least 100 mg of product per mL of load fluid. Purified product can be recovered from up to 50 CVs of load fluid passed through the medium.

High load challenges are also possible with weak partitioning mode. In one embodiment, the load onto the medium may be at a load challenge of at least 10 mg of product per mL of medium. In other embodiments, the loading of the product onto the medium is at least 50 mg of product per mL of medium. It certain embodiments, the loading of the product onto the medium is at least 100 mg of product per mL of medium. In other embodiments, the load onto the medium may be at a load challenge of at least 500 mg of product per mL of medium. In yet other embodiments, the load onto the medium may be at a load challenge of at least 1000 mg of product per mL of medium.

5. Removal of Impurities

Weak partitioning mode has been shown to be useful for removing all types of impurities from product preparations, including host cell proteins, nucleic acids, product variants, including aggregated product and high molecular weight species, endotoxins, viruses, and Protein A contaminants from prior purification steps.

In one embodiment of the invention, the concentration of host cell proteins present in the purified product is no more than about 500 ng host cell proteins per mg of product. In other embodiments, the concentration of host cell proteins can be reduced to no more than 250 ng per mg of product, and in other embodiments, to no more than 100 ng per mg of product. In certain embodiments, the log removal value of host cell proteins is at least 1.0, in other embodiments, the log removal value of host cell proteins is at least 2.0, and in other embodiments, the log removal value of host cell proteins is at least 3.0.

In one embodiment of the invention, the concentration of Protein A present in the purified product is no more than about 100 ng Protein A per mg of product. In some embodiments, the concentration of Protein A can be reduced to no more than 50 ng per mg of product, and in other embodiments, to no more than 10 ng per mg of product. In certain embodiments, the log removal value of Protein A is at least 1.0, and in other embodiments, the log removal value of Protein A is at least 2.0, and in other embodiments, the log removal value of Protein A is at least 3.0.

In another embodiment of the invention, viral impurities are removed from the purified product. In certain embodiments, the log removal value of viruses is greater than 1.0, in other embodiments, greater than 2.0, and in other embodiments, greater than 3.0.

In some embodiments of the invention, nucleic acid impurities are removed from the purified product. In certain embodiments, the amount of nucleic acids present in the purified product can be reduced to no more than 1 ng nucleic acids per mg of product.

In additional embodiments, the concentration of protein variants in the purified product is no more than about 10%. In some embodiments, the concentration of protein variants can be reduced to no more than about 5%, in some embodiments, to no more than 2%, and in some embodiments, to no more than 0.5%.

Under the stringent binding conditions of weak partitioning mode, the separation medium removes at least 90% of host cell protein, nucleic acid, protein variant, endotoxin, and Protein A impurities. In some embodiments, the medium removes at least 99% of the impurities, and in other embodiments, the medium removes at least 99.9% of the impurities.

6. Additional Optional Steps

The purification method of the invention can be used in combination with other protein purification steps. In one embodiment of the invention, one or more steps preceding the weak partitioning step may be desirable to reduce the load challenge. In another embodiment of the invention, one or more purification steps following the weak partitioning step may be desirable to remove additional contaminants or impurities.

The weak partitioning purification procedure described may optionally be combined with other purification steps, including but not limited to, Protein A chromatography, affinity chromatography, hydrophobic interaction chromatography, immobilized metal affinity chromatography, size exclusion chromatography, diafiltration, ultrafiltration, viral removal filtration, and/or ion exchange chromatography. The optional purification steps preceding and/or following the weak partitioning step may also be operated in weak partitioning mode, or in other modes, such as bind-elute mode or flow-through mode.

In one embodiment, prior to the weak partitioning purification step, the harvest media may optionally be initially purified by a Protein A chromatography step. For example, PROSEP-A™ (Millipore, U.K.), which consists of Protein A covalently coupled to controlled pore glass, can be employed. Other useful Protein A formulations include Protein A Sepharose FAST FLOW™ (Amersham Biosciences, Piscataway, N.J.), TOYOPEARL™ 650M Protein A (TosoHaas Co., Philadelphia, Pa.), and MABSELECT™ columns (Amersham Biosciences, Piscataway, N.J.).

7. Zwitterionic Buffers Used in Tandem with Protein a Chromatography and Ion Exchange Chromatography In certain embodiments, a product-containing fluid is eluted from a Protein A column using an elution buffer of low ionic strength. The pH and conductivity of the product-containing fluid is then adjusted using a neutralization buffer, which results in no more than 20 mM of the ionic strength of the product-containing fluid. The resulting load fluid is then passed through an anion exchange medium or hydroxyapatite medium operating under conditions of weak partitioning mode. In certain embodiments, the load fluid is passed through an anion exchange medium without the need for diafiltration. In some embodiments, the pH and conductivity of the product-containing fluid is adjusted using a neutralization buffer which results in no more than 40 mM of the ionic strength of the product-containing fluid. In other embodiments, the pH and conductivity of the product-containing fluid is adjusted using a neutralization buffer that results in no more than 60 mM of the ionic strength of the product-containing fluid. In yet other embodiments, the pH and conductivity of the product-containing fluid is adjusted using a neutralization buffer that results in no more than 80 mM of the ionic strength of the product-containing fluid.

Buffers that can be used for elution from the Protein A column include buffers comprising molecules with a charged anionic group with a pKa of 2-5. Such elution buffers could further comprise molecules with a charged cationic group with a pKa of 6.5-10. In one embodiment, the elution buffer comprises molecules which are zwitterions at pHs between 4 and 9, such as glycine; 1,4-piperazinebis-(ethanesulfonic acid); glycylglycine; cyclopentanetetra-1,2,3,4-carboxylic acid; N,N-bis(2-hydroxyethyl)-2-aminoethanesulfonic acid; 2-(N-morpholino)propane-sulfonic acid; N-tris(hydroxylmethyl)methyl-2-aminoethane sulfonic acid; N-2-hydroxyethylpiperazine-N'-2-ethanesulfonic acid; 4-(2-hydroxyethyl)-1-piperazinepropane sulfonic acid; N-tris(hydroxymethyl) methylglycine; glycinamide; N,N-bis(2-hydroxyethyl) glycine; N-tris(hydroxymethyl)methyl-2-aminopropane sulfonic acid; or N-glycyl-glycine.

The elution of a Protein A column with a zwitterionic buffer provides the advantage of low ionic strength upon some degree of neutralization. The low ionic strength of the buffer does not adversely impact the operation of subsequent ion exchange columns, including hydroxyapatite columns. High levels of ionic strength will decrease the binding of impurities to ion exchange columns, which may decrease the overall efficiency of the purification. Lower ionic strength solutions are preferred for loads onto ion exchange columns, as the ionic strength can be raised easily with the addition of concentrated salt solutions; decreasing the ionic strength of solutions is not facile. Surprisingly, there exist buffers that have a low pKa that allow use at low pH levels useful in Protein A elution steps, but that also have a second pKa that allow use at higher pH levels useful in ion exchange chromatography; these buffers, if used at a proper second pH, have little effective charge during the operation of the ion exchange step subsequent to the Protein A step.

A zwitterionic buffer that has a pKa near that of the elution pH preferred for Protein A (between pH 2 and 5, preferably between 2.5 and 4.0) allows the buffer to be used to maintain the pH near the buffer's pI and to elute the column. Zwitterionic buffers that also have a pKa near that of the operation of a subsequent ion exchange column (pH 5.5 to 11) would allow the buffer to control the pH in this pH range as well as in the Protein A elution pH range. The use of a single compound for both elution of the Protein A column at low pH and for maintenance of the higher pH useful in ion exchange chromatography simplifies the operation of both steps, and also simplifies the composition of the product pool after neutralization.

In a further embodiment of the invention, a zwitterionic buffer with pKa1 and pKa2 can elute a Protein A column at pH levels within one pH unit of pKa1. Further, if the Protein A pool is neutralized with a basic solution of the zwitterionic buffer to a second pH within one pH unit of pKa2, the zwitterionic buffer will be able to maintain the pH of the solution. If the second pH is below that of pKa2, the buffer remains zwitterionic and contributes little to the overall ionic strength of the solution. For example, a zwitterionic buffer with concentration x at a pH equal to the pKa2 will contribute to the overall ionic strength only x/2. A zwitterionic buffer with concentration x at 1 pH unit below the pKa2 of the buffer will have a ionic strength of one-tenth of x. This reduction in ionic strength is significantly useful for operation of ionic exchange chromatography.

The existence of buffers that have a pKa1 useful for elution of Protein A columns and a pKa2 useful for operation of ion exchange chromatography is not obvious, in that the pKa1 of these buffers is not commonly reported. Buffers are commonly used at pH levels near that of pKa2, and are not known by those skilled in the art of chromatography to be useful for elution from a Protein A column. Further, while the utility of these buffers for elution from Protein A chromatographic columns is not generally realized, it is also not realized that these zwitterionic buffers would have additional utility as buffers for ion exchange columns subsequent to Protein A columns because they contribute less ionic strength to the neutralized Protein A pool.

C. Examples

The following examples are offered for illustrative purposes only.

Examples are provided for three modes of chromatography (anion exchange, hydrophobic interaction, and hydroxyapatite), using three different monoclonal antibodies. Four separate series of experiments are described, each representing a different pairing of the chromatography mode and the monoclonal antibody to be purified. The initial screening studies are presented first, which determine the partition coefficient and/or the concentration of product bound to the resin under various solution conditions, thus defining the operating regions of weak partitioning (WP) and flow-through (FT) modes. Several column studies are then summarized, with data on product recovery and impurity removal. The product recoveries are excellent for the WP column runs, and the impurity levels are lower than in the corresponding FT studies. The WP runs were conducted with higher load challenges to the resin than the FT studies.

The levels of Protein A residuals in the test samples were measured using a Protein A enzyme-linked immunosorbent assay (ELISA). The amount of high molecular weight aggregate was measured using an analytical size exclusion chromatography (SEC) assay. The levels of host cell proteins (HCPs) were measured using a HCP ELISA. All screening and column studies were conducted at room temperature.

Series 1—Anion Exchange Using TMAE-HiCap (M) and Mab-AAB

Experiment 1.1

High Throughput Screen to Establish WP and FT Conditions

A high throughput screen (HTS) was performed to identify the weak partitioning and flow-through conditions for Mab-AAB with TMAE-HiCap (M) medium. This screen varied the concentration of sodium chloride and pH to determine their effect on the extent of binding of MAB-AAB and process related impurities (Protein A and HCP) to the TMAE medium.

50 μL of TMAE HiCap medium was added to each well of a 96 well filter plate. Each well was equilibrated in solutions made up 50 mM glycine and a variable amount of Tris buffer (depending upon the amount needed for neutralization to the pH specified in Table 1.1.1) and sodium chloride (specified in Table 1.1.2). The pH ranged from 7.6 to 9.0 and the sodium chloride ranged from 0 mM to 80 mM.

The buffer solutions used in each row were diluted on an automated pipetting system (Tecan 100 RST). The stock solution for the buffers were made from 500 mM glycine acidified with HCl to pH 3.0, and subsequently neutralized with 2M Tris Base to the pH levels indicated in Table 1.1.1. This titration resulted in a level of Tris that depended upon the pH of the buffer. The buffer pH was measured at a 1 to 10 dilution of the stock buffer concentration, which corresponded to the dilution made by the automated pipetting system. As a result of the glycine acidification to pH 3.0, the buffer contributes about 10 mM of ionic strength to the final solution. Two load challenges were made to the resin: 5 mg/mL to measure the partition coefficient, K, and 122 mg/mL, to measure the capacity of the resin for removal of impurities and the bound product, Q, in equilibrium with a protein solution at a concentration approximately equal to the column load concentration.

TABLE 1.1.1

| Buffer type and pH target in each well |
|---|
| All columns |

| | |
|---|---|
| A | 50 mM Glycine, 8.8 mM Tris, pH 7.6 |
| B | 50 mM Glycine, 13.6 mM Tris, pH 7.8 |
| C | 50 mM Glycine, 16.0 mM Tris, pH 8.0 |
| D | 50 mM Glycine, 19.6 mM Tris, pH 8.2 |
| E | 50 mM Glycine, 28.4 mM Tris, pH 8.4 |
| F | 50 mM Glycine, 37.2 mM Tris, pH 8.6 |
| G | 50 mM Glycine, 64.0 mM Tris, pH 8.8 |
| H | 50 mM Glycine, 100 mM Tris, pH 9.0 |

TABLE 1.1.2

NaCl levels (in mM) and protein challenges (mg/mL) in each well

| | All Rows | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| NaCl (mM) | 0 | 10 | 20 | 40 | 60 | 80 | 0 | 10 | 20 | 40 | 60 | 80 |
| MAB-AAB (mg/mL) | 5 | 5 | 5 | 5 | 5 | 5 | 132 | 132 | 132 | 132 | 132 | 132 |

In the first stage of the HTS experiment, each well was equilibrated in the conditions of NaCl and pH as described in Tables 1.1.1 and 1.1.2 in a phase volume ratio of 6:1 (300 uL solution: 50 uL resin). The plate was shaken for 20 minutes, allowing equilibrium to be reached. The solution was then removed by centrifuging the filter plate. This equilibration cycle was repeated three times.

In the second stage, the resin in each well was challenged with a concentrated MAb-AAB solution to 5 mg/mL of resin with a volume ratio of 6:1 (300 uL solution: 50 uL resin) at the appropriate NaCl concentration and pH. A 36 mg/mL solution of Mab-AAB in 1 mM HEPES, 10 mM NaCl, pH 7.0 spiked with 300 ppm of Protein A was used as stock solution. The loaded plate was shaken for 20 minutes, allowing the resin and solution to equilibrate. The supernatant was removed from the filter plate by centrifugation and collected into a collection plate. The protein concentration in the supernatant in each well was determined by absorbance at A280 nm.

Figure 7:
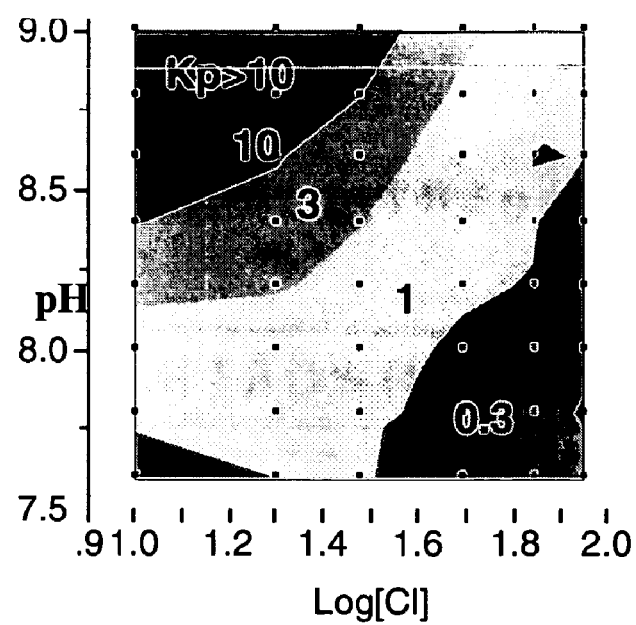
FIG. 7 shows a contour plot of Kp vs. pH and the total chloride concentration from the low concentration dataset, as described in Experiment 1.1.

In the third stage, resin was washed by adding solutions of the specified NaCl and pH conditions listed in Table 1.1.2. The supernatant was removed after shaking for 20 minutes. In the fourth stage, 2M NaCl was added to remove the remaining protein that was bound to the resin. The partition coefficients were calculated for each well using the mass eluted from stages 3 and 4 and the product concentration from stage 2, and are shown in Table 1.1.3. A contour plot of the log of the partition coefficient as a function of pH and chloride is shown in FIG. 7.

TABLE 1.1.3

Partition Coefficients (K) for the 96 well HTS screen for MAB-AAB

|   | 1 | 2 | 3 | 4 | 5 | 6 | 7 | 8 | 9 | 10 | 11 | 12 |
|---|---|---|---|---|---|---|---|---|---|----|----|----|
| A | 0.22 | 0.32 | 0.35 | 0.17 | 0.24 | 0.23 | 0.21 | 0.24 | 0.21 | 0.19 | 0.17 | 0.16 |
| B | 0.37 | 0.36 | 0.38 | 0.25 | 0.24 | 0.08 | 0.28 | 0.26 | 0.22 | 0.24 | 0.18 | 0.16 |
| C | 0.63 | 0.48 | 0.47 | 0.27 | 0.15 | 0.20 | 0.31 | 0.28 | 0.26 | 0.20 | 0.23 | 0.16 |
| D | 1.24 | 1.12 | 0.68 | 0.36 | 0.30 | 0.17 | 0.42 | 0.39 | 0.34 | 0.23 | 0.23 | 0.18 |
| E | 3.24 | 1.89 | 1.05 | 0.59 | 0.35 | 0.15 | 0.68 | 0.58 | 0.41 | 0.29 | 0.21 | 0.18 |
| F | 8.37 | 3.37 | 1.56 | 0.61 | 0.31 | 0.32 | 0.87 | 0.74 | 0.51 | 0.32 | 0.25 | 0.21 |
| G | 18.36 | 9.49 | 3.16 | 0.82 | 0.49 | 0.34 | 0.91 | 0.88 | 0.69 | 0.39 | 0.24 | 0.20 |
| H | 125.73 | 23.79 | 6.58 | 1.23 | 0.58 | 0.43 | 1.18 | 1.02 | 0.78 | 0.42 | 0.27 | 0.24 |

As shown in Table 1.1.3, the Kp value can be used to describe regions where MAB-AAB binds to the TMAE medium with different strengths. These regions are more clearly visualized in FIG. 7. The strength of MAB-AAB binding to TMAE medium can be manipulated by varying conditions of pH and chloride concentration into flow-through (K=<0.1), weak partitioning (0.1<K<20), and binding zones (K=>20).

Figure 8:
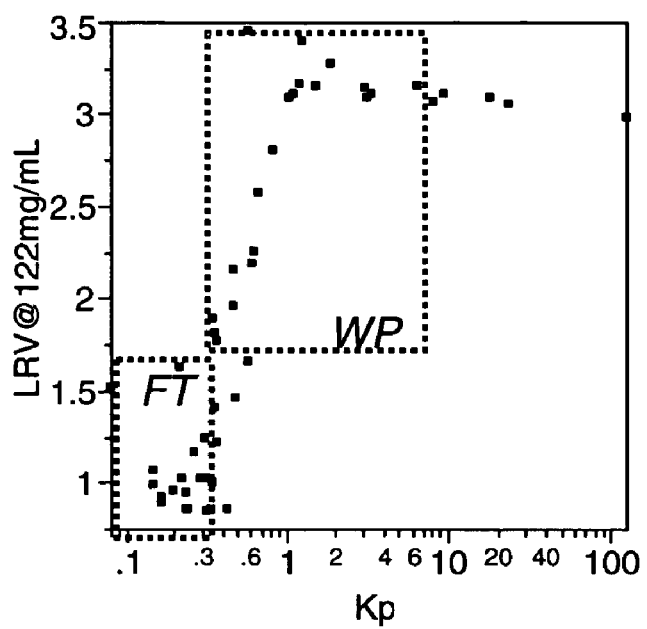
FIG. 8 shows Protein A removal as a function of the partition coefficient, Kp, as described in Experiment 1.1. The log removal value increases with Kp. Flow-through mode is indicated by the dashed box with "FT", while weak partitioning mode is indicated by the dashed box with "WP."

The supernatant from the load stage of all wells from each zone were sampled and submitted for Protein A analysis. The assay results of these samples are summarized in Table 1.1.4. There is a region of pH and conductivity where the TMAE chromatography step provides very significant removal of Protein A with limited protein loss to the resin. This region was found to be closely correlated to the partition coefficient value, Kp, and not any specific pH or chloride concentration (see FIG. 8).

Experiment 1.2

Column Runs Under Flow-through Conditions

The following experiment was performed in the flow-through (FT) mode, where the Mab-AAB interacts only very weakly with the column. Two runs were performed with load challenges of 110 mg/ml and 200 mg/ml of resin.

For all TMAE (HiCapM) anion exchange chromatography runs described in the Series 1 experiments, the following conditions were used (exceptions are noted in the individual experimental descriptions).

Operational flow rate—150-300 cn/hr
Equilibration 1—50 mM Tris, 2.0 M NaCl, pH 7.5 (5 column volumes)
Equilibration 2—as specified, approximately equivalent to the load pH and chloride content
Post load wash—as specified, approximately equivalent to the load pH and chloride content
Strip buffer—50 mM Tris, 2.0 M NaCl, pH 7.5 (5 column volumes)

Mabselect Protein A Chromatography

The culture containing the monoclonal antibody was purified at Pilot scale using a MabSelect column (2,389 mL) connected to a Millipore K-prime 400 chromatography system. A Mabselect Protein A column was equilibrated with 5 column volumes of 50 mM Tris/150 mM NaCl, pH 7.5 at a flow rate of 300 cm/hr. The column was then loaded at a load of approximately 40 mg product/ml resin. This was followed

TABLE 1.1.4

Protein A Log Removal Values (LRV) for MAB-AAB binding data from HTS screen

|   | 1 | 2 | 3 | 4 | 5 | 6 | 7 | 8 | 9 | 10 | 11 | 12 |
|---|---|---|---|---|---|---|---|---|---|----|----|----|
| A | 2.11 | 1.89 | 2.12 | 1.85 | 1.22 | 1.00 | 1.63 | 1.02 | 1.00 | 0.92 | 0.85 | 1.02 |
| B | 2.79 | 2.37 | 2.42 | 1.96 | 1.23 | 1.13 | 1.77 | 1.81 | 1.22 | 0.85 | 0.94 | 1.52 |
| C | >3.05 | >3.03 | 2.74 | 2.16 | 1.37 | 1.11 | 2.25 | 2.15 | 1.96 | 1.16 | 1.06 | 0.95 |
| D | >3.41 | >2.98 | >3.06 | 2.50 | 1.94 | 1.18 | 3.39 | 3.11 | 2.57 | 1.41 | 1.02 | 0.89 |
| E | >2.87 | >2.93 | >3.01 | >2.95 | 2.13 | 1.75 | >3.09 | 3.27 | 3.09 | 1.66 | 1.89 | 0.99 |
| F | >2.64 | >2.89 | >2.99 | >3.11 | 2.29 | 1.82 | >3.07 | >3.11 | >3.15 | 2.19 | 1.24 | 0.84 |
| G | >2.33 | >2.58 | >2.89 | >3.07 | 2.41 | 2.14 | >3.09 | >3.11 | >3.14 | 2.80 | 1.46 | 0.85 |
| H | >1.63 | >2.36 | >2.76 | >3.01 | 2.86 | 2.37 | >2.98 | >3.05 | >3.15 | 3.16 | 3.45 | 0.85 | by a 5CV wash in 1M NaCl, 50 mM Tris, pH 7.5 and a 5CV wash containing 10 mM Tris, 75 mM NaCl, pH 7.5 wash. The column was then eluted using 50 mM glycine, 75 mM NaCl, pH 3.0. The product pool was neutralized to pH 7.6 using 2M Tris pH 8.5. The neutralized peak had a chloride concentration of approximately 90 mM.

TMAE HiCap (M) Chromatography

The neutralized Protein A pool was further purified over the TMAE step with the equilibration, load, and wash solutions at pH 7.5 with 50 mM Tris and 75 mM sodium chloride. 5 column volumes of wash were used. The column dimensions and load challenges for these two studies were: Run 1: 7.0 cm diameter×20.6 cm bed height (volume—793 mL) with a load concentration of 11.9 mg/mL, and Run 2: 7.0 cm diameter×13 cm bed height (volume—500 mL) with a load concentration of 17.6 mg/mL.

These load conditions were in the flow-through (FT) region (Table 1.2.1). Batch binding studies were used to measure the partition coefficient (Kp) and the bound product was determined by protein in the column strip by using UV absorbance. This method of determining the bound product typically underestimates the amount of product bound during the load due to isocratic elution of the product during the wash. The levels of Protein A, HCP and HMW in the load and product pool were measured, and the extent of removal calculated. The results are presented in Table 1.2.1. There is poor removal of Protein A and HMW, and modest reduction in HCP levels.

material for these runs. The partially purified antibody pool from the Protein A step was further purified over the TMAE column. The load to the TMAE column was in 50 mM Tris, pH 8.2. The column diameter was 0.5 cm and the bed height was 10 cm bed height (volume—2.0 mL). The column was challenged to a load of 500 mg/mL resin, with a load concentration of 27.7 mg/mL.

The column was equilibrated with 5 column volumes of a solution containing 50 mM Tris, 2M NaCl pH 7.5 followed by another equilibration step comprising a 50 mM Tris, pH 8.2 solution. The column was then loaded to 500 mg product/ml resin with the neutralized Protein A peak from the previous step and the product was recovered in the column effluent during the load cycle and some column volumes of the wash fraction.

These load conditions are in the weak partitioning region. Batch binding studies were used to measure the partition coefficient (Kp), and product binding at high protein concentrations. At pH 8.2, and an approximate chloride content of 12 mM, the partition coefficient, Kp, is estimated to be 1.9 (from interpolation of the dataset from the HTS screen).

The levels of HCP and Protein A were measured in three fractions during the loading stage representing load challenges of approximately 250, 375, and 500 mg/ml of resin.

TABLE 1.2.1

Removal of HCP, Protein A, and HMW under flow-through conditions

| Run | Load Challenge (mg/mL) | Partition Coefficient (Kp) | Bound Product (mg/mL resin) | HCP (LRV) | Protein A (LRV) | HMW (Fold) | Recovery (%) |
|---|---|---|---|---|---|---|---|
| 1 | 110 | 0.17 | 1.4 | 2.3 | 0.1 | — | 96 |
| 2 | 200 | 0.17 | 3.3 | 2.0 | <0.1 | 1.5 | 96 |

* Impurity levels were 38.5 ppm ProA and 51,943 ppm HCP (Run 1), 8.8 ppm ProA and 25,398 ppm HCP (Run 2).

Experiment 1.3

Column Runs Under Weak Partitioning Conditions (High Product Challenge)

TMAE (HiCap M) Anion Exchange Chromatography

Several Mabselect Protein A runs were performed essentially as described in Experiment 1.2 to generate the load The results from experiment 1.3 are presented in Table 1.3.1. These results demonstrate that very high product challenges can be achieved in weak partitioning mode, without breakthrough of impurities. Excellent reduction in both HCP and Protein A was achieved, along with 50% reduction in HMW content. In comparison to the results for operation in the flow-through mode in Table 1.2.1, the removal of impurities was much better in the weak partitioning mode.

TABLE 1.3.1

Removal of HCP, Protein A and HMW for a 500 mg/mL TMAE load challenge

|  | Early fraction (250 mg/ml) | Middle fraction (375 mg/ml) | Late fraction (500 mg/ml) | Final product pool (ppm) |
|---|---|---|---|---|
| Residual HCP ppm (ng/mg product) | <7.6 | <7.6 | <7.6 | <7.6 |
| HCP Log Removal Value (LRV) | >3.5 | >3.5 | >3.5 | >3.5 |
| Residual Protein A ppm (ng/mg product) | 0.3 | Not determined | 0.1 | 0.6 |
| ProA Log Removal Value (LRV) | 2.9 | Not determined | 2.3 | 2.5 |
| HMW | Not determined | Not determined | Not determined | 2 fold removal |

*The impurities in the load were 25,398 ppm of HCP, 99.5 ppm of Protein A, and 2.3% HMW.

Experiment 1.4

Column Runs Under Weak Partitioning Conditions (Robustness Studies)

To further confirm the performance of the TMAE column in the region of weak partitioning, several runs were designed varying the pH and NaCl concentration in the load to test process robustness. All runs were performed at a load challenge of 250 mg/ml resin. Several Mabselect Protein A runs were performed essentially as described in Experiment 1.2 to generate the load material for these runs. The only factor varied in those runs was the sodium chloride concentration in the Protein A elution, which was varied to match the NaCl concentration in the TMAE load for a particular experiment. The columns were equilibrated with Equil 2 buffers and washed with Wash buffers which had approximately the same pH and sodium chloride content of the load.

These load conditions are in the weak partitioning region. Batch binding studies were used to measure the partition coefficient (Kp). The runs are ranked by the partition coefficients listed in Table 1.4.1. The bound product was determined by measuring the protein in the column strip using UV absorbance, and ranges from 7.8-25.3 mg/mL. Protein A, HCP and HMW results from these experiments are also presented in Table 1.4.1. The removal of all impurities was found to be robust in operating ranges which cover 13.5-38.8 mM total chloride and pH 7.8-8.4.

Series 2—Anion Exchange using TMAE-HiCapM and Mab-IMA

Experiment 2.1

High Throughput Screening to Establish WP and FT Conditions

A high throughput screen (HTS) was performed to identify the weak partitioning and flow-through conditions for Mab-IMA with TMAE-HiCap (M) medium. This screen varied the concentration of sodium chloride and pH to determine their effect on the extent of binding of MAB-IMA and process related impurities (Protein A and HCP) to the TMAE medium. 100 µL of TMAE HiCap medium was added to each well of a 96 well filter plate. Each well was equilibrated in solutions made up of 25 mM buffer no more than 1 pH unit away from the buffer pKa (Table 2.1.1) and the appropriate level of sodium chloride (Table 2.1.2). The pH ranged from 7.00 to 8.75 and the sodium chloride concentration ranged from 1 mM to 190 mM.

All buffers were titrated to the target pH using 12M HCl. As a result of different buffering species required different levels of titrant, the chloride concentration varied from well to well depending on which buffer was used for that well. The amount of Cl— needed to titrate the buffer to the target pH was calculated using the Henderson-Hasselbach equation and added to the total Cl— contributed from both the NaCl and the amount in the load material. The calculated Cl— level for each well in the experiment is listed in Table 2.1.3.

TABLE 1.4.1

Process robustness studies on removal of HCP, Protein A, and HMW in weak partitioning mode

| NaCl Concentration (mM) | Kp | Bound Product (mg/mL) | pH | HCP in Load (ppm) | Protein A in load (ppm) | HCP (LRV) | Protein A (LRV) | HMW (Fold) | Recovery (%) |
|---|---|---|---|---|---|---|---|---|---|
| 38.8 | 0.26 | 9.4 | 7.8 | 26,391 | 493.5 | 3.7 | 1.8 | 2.0 | 92 |
| 13.5 | 0.41 | 7.9 | 7.8 | 12,821 | 69.2 | 3.3 | >1.9 | 1.8 | 87 |
| 27.4 | 0.50 | 8 | 8.0 | 23,465 | 252 | 3.6 | 2.2 | 3.2 | 91 |
| 18.5 | 0.73 | 7.8 | 8.0 | 21,626 | 308 | 3.7 | >3.2 | 2.9 | 90 |
| 23.5 | 0.80 | 9.5 | 8.1 | 18,004 | 343 | 3.2 | >3.2 | 3.5 | 94 |
| 27.7 | 0.86 | 9.5 | 8.2 | 24,821 | 280 | 3.6 | >3.2 | 2.6 | 99 |
| 18.5 | 1.48 | 10 | 8.2 | 17,669 | 252 | 3.7 | >3.1 | 3.9 | 95 |
| 22.0 | 5.35 | 25.3 | 8.4 | 29,293 | 533 | 3.6 | >2.9 | 2.3 | 90 |

\* Impurity levels were 38.5 ppm ProA and 51,943 ppm HCP (Run 1), 8.8 ppm ProA and 25,398 ppm HCP (Run 2).
+ includes the Cl— ion contribution from NaCl, buffers and titrants Summary From this study, it can be seen that Protein A removal (LRV) varies strongly with Kp, while HCP LRV is excellent at all the values of Kp at or above 0.26, but much reduced at Kp=0.17 (under flow-through conditions). Host cell protein removal is over one log lower for flow-through conditions compared to weak partitioning conditions, even for a reduced load challenge. The bound product ranges from 7.8-25 mg/mL for these weak partitioning conditions on this combination of resin and monoclonal antibody. The partition coefficient appears to be optimal between 0.41<Kp<5.4. It does not appear to be optimal at Kp=0.17 and a bound product of 1.4-3.3 mg/mL, the conditions of Experiment 1.2.

TABLE 2.1.1

Buffer type and pH target in each well

All columns

| A | Ethanolamine (pH = 8.75) |
| B | Tris (pH = 8.5) |
| C | Tris (pH = 8.25) |
| D | Tris (pH = 8.0) |
| E | Tris (pH = 7.75) |
| F | Tris (pH = 7.5) |
| G | Bis-Tris (pH = 7.25) |
| H | Bis-Tris (pH = 7.0) |

TABLE 2.1.2

NaCl levels in each well (in mM)

|  | 1 | 2 | 3 | 4 | 5 | 6 | 7 | 8 | 9 | 10 | 11 | 12 |
|---|---|---|---|---|---|---|---|---|---|---|---|---|
| All rows | 1 | 5 | 10 | 15 | 25 | 35 | 50 | 75 | 100 | 125 | 150 | 190 |

TABLE 2.1.3

Cl- levels in each well (in mM)

|  | 1 | 2 | 3 | 4 | 5 | 6 | 7 | 8 | 9 | 10 | 11 | 12 |
|---|---|---|---|---|---|---|---|---|---|---|---|---|
| A | 22 | 26 | 31 | 36 | 46 | 56 | 71 | 96 | 121 | 146 | 171 | 211 |
| B | 8 | 12 | 17 | 22 | 32 | 42 | 57 | 82 | 107 | 132 | 157 | 197 |
| C | 11 | 15 | 20 | 25 | 35 | 45 | 60 | 85 | 110 | 135 | 160 | 200 |
| D | 15 | 19 | 24 | 29 | 39 | 49 | 64 | 89 | 114 | 139 | 164 | 204 |
| E | 18 | 22 | 27 | 32 | 42 | 52 | 67 | 92 | 117 | 142 | 167 | 207 |
| F | 21 | 25 | 30 | 35 | 45 | 55 | 70 | 95 | 120 | 145 | 170 | 210 |
| G | 8 | 12 | 17 | 22 | 32 | 42 | 57 | 82 | 107 | 132 | 157 | 197 |
| H | 11 | 15 | 20 | 25 | 35 | 45 | 60 | 85 | 110 | 135 | 160 | 200 |

In the first stage of the HTS experiment, each well was equilibrated in the conditions of NaCl and pH as described in Tables 2.1.1 and 2.1.2 in a phase volume ratio of 3:1 (300 uL solution: 100 uL resin). The plate was shaken for 20 minutes, allowing equilibrium to be reached. The solution was then removed by centrifuging the filter plate. This equilibration cycle was repeated three times.

In the second stage, the resin in each well was challenged with a concentrated MAb-IMA solution to 3 mg/mL of resin with a volume ratio of 3:1 (300 uL solution: 100 uL resin) at the appropriate NaCl concentration and pH. A 30 mg/mL solution of Mab-IMA in 1 mM Mes, 15 mM NaCl, pH 6.5 with 300 ppm of Protein A was used as stock solution. The loaded plate was shaken for 20 minutes, allowing the resin and solution to equilibrate. The supernatant was removed from the filter plate by centrifugation and collected into a collection plate. The protein concentration in the supernatant in each well was determined by absorbance at A280 nm. Any decrease in Protein A and/or HCP levels indicates a condition conducive to purification.

Figure 9:
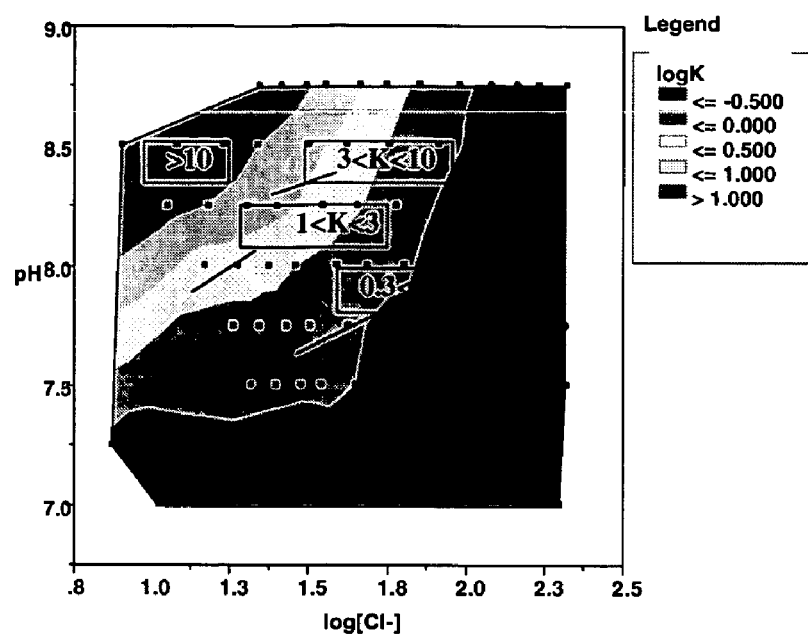
FIG. 9 shows a contour plot of $\log_{10}$Kp vs. pH and the log of the total chloride concentration, as described in Experiment 2.1.

In the third stage, resin was washed by adding solutions of the specified NaCl and pH conditions listed in Table 2.1.2. The supernatant was removed after shaking for 20 minutes. In the fourth stage, 2M NaCl was added to remove the remaining protein that was bound to the resin. The partition coefficients were calculated for each well using the mass eluted from stages 3 & 4 and the product concentration from stage 2, and are shown in Table 2.1.4. A contour plot of the log of the partition coefficient as a function of pH and chloride is shown in FIG. 9.

TABLE 2.1.4

Partition Coefficients (Kp) for the 96 well HTS screen for MAB-IMA

|  | 1 | 2 | 3 | 4 | 5 | 6 | 7 | 8 | 9 | 10 | 11 | 12 |
|---|---|---|---|---|---|---|---|---|---|---|---|---|
| A | 34.5 | 20.2 | 11.4 | 7.2 | 3.5 | 1.8 | 0.8 | 0.4 | 0.3 | 0.3 | 0.2 | 0.2 |
| B | 97.1 | 42.4 | 19.3 | 9.9 | 4.3 | 2.2 | 1.0 | 0.4 | 0.3 | 0.2 | 0.2 | 0.2 |
| C | 14.8 | 9.4 | 5.8 | 4.2 | 2.0 | 1.1 | 0.5 | 0.3 | 0.3 | 0.2 | 0.2 | 0.2 |
| D | 1.8 | 1.6 | 1.3 | 1.0 | 0.7 | 0.5 | 0.4 | 0.2 | 0.2 | 0.2 | 0.2 | 0.2 |
| E | 0.7 | 0.7 | 0.7 | 0.6 | 0.4 | 0.3 | 0.3 | 0.2 | 0.2 | 0.2 | 0.2 | 0.2 |
| F | 0.4 | 0.4 | 0.4 | 0.4 | 0.3 | 0.3 | 0.3 | 0.2 | 0.2 | 0.2 | 0.2 | 0.2 |
| G | 0.2 | 0.2 | 0.3 | 0.2 | 0.2 | 0.2 | 0.2 | 0.2 | 0.2 | 0.2 | 0.2 | 0.2 |
| H | 0.2 | 0.2 | 0.3 | 0.2 | 0.2 | 0.2 | 0.2 | 0.2 | 0.2 | 0.2 | 0.2 | 0.2 |

As shown in Table 2.1.4, the Kp value can be used to describe regions where MAB-IMA binds to the TMAE medium with different strengths. These regions are more clearly visualized in FIG. 9. The strength of MAb-IMA binding to TMAE medium can be manipulated by varying conditions of pH and chloride concentration into flow-through ($Kp \leq 0.1$), weak partitioning ($0.1 < Kp < 20$), and binding zones ($Kp \geq 20$).

The supernatant from the load stage of several wells from each zone were sampled and submitted for Protein A analysis. The load had 300 ppm of Protein A. The assay results of these samples are summarized in Table 2.1.5. There is a region of pH and conductivity where the TMAE chromatography step provides very significant removal of Protein A with limited protein loss to the resin. This region is found to be closely correlated to the partition coefficient value, Kp, and not any specific pH or chloride concentration.

TABLE 2.1.5

Protein A residual levels and MAB-IMA binding data from HTS screen

| pH | Cl- (mM) | Kp (predicted) | Protein A (ppm) |
|---|---|---|---|
| 8.5 | 12 | 42.4 | <28 - BLOQ |
| 8.5 | 32 | 4.3 | <7 - BLOQ |
| 8.25 | 35 | 2.0 | <5 - BLOQ |
| 8.25 | 45 | 1.13 | <4 - BLOQ |
| 8.0 | 39 | 0.7 | <4 - BLOQ |
| 8.25 | 60 | 0.5 | <4 - BLOQ |
| 7.75 | 42 | 0.4 | <4 - BLOQ |
| 7.5 | 45 | 0.3 | 35 |
| 8.0 | 64 | 0.3 | 63 |
| 8.25 | 110 | 0.3 | 190 |
| 7.25 | 32 | 0.2 | 90 |
| 8.0 | 89 | 0.2 | 177 |
| 8.75 | 121 | 0.3 | 217 |
| 7.75 | 92 | 0.2 | 187 |
| 7.5 | 120 | 0.2 | 219 |
| 7.25 | 107 | 0.2 | 224 |

Predicted Kp values are derived from a response surface fit to the HTS screen, and subsequent prediction of the Kp based on this regression model.

Experiment 2.2

Column Runs Under FT Conditions Using TMAE-HiCapM and Mab-IMA

The following experiment was performed in the flow-through (FT) mode, where the Mab-IMA interacts only very weakly with the column. Four runs were conducted, with product challenges of 109-275 mg/ml of resin.

TMAE (HiCap M) Anion Exchange Chromatography

For all TMAE (HiCapM) anion exchange chromatography steps described in the Experiment 2 series, the following conditions were used (exceptions are noted in the individual experimental descriptions).

Operational flow rate—150-300 cm/hr
Equilibration 1—50 mM Tris, 2.0 M NaCl, pH 7.5 or 8.0 (5 column volumes)
Equilibration 2—75 mM NaCl, 50 mM Tris, pH 7.5 (runs 3 and 4 contained 50 mM Glycine)
Post load wash—75 mM NaCl, 50 mM Tris, pH 7.5 (runs 3 and 4 contained 50 mM Glycine)
Strip buffer—50 mM Tris, 2.0 M NaCl, pH 7.5 or 8.0 (5 column volumes)

Several Mabselect Protein A runs were performed essentially as described in Experiment 1.2 to generate the load material for these runs. The partially purified antibody pools from the previously described Protein A step were further purified over the anion exchange step in a flow-through (FT) mode. Column diameters ranged from 1.0-3.2 cm and the column heights were 7.2-8.5 cm.

The columns were equilibrated with 5 column volumes of a solution containing 50 mM Tris, 2M NaCl pH 7.5 followed by another equilibration step comprising a 50 mM Tris, pH 7.5 solution. The columns were then loaded to between 109 mg/mL and 275 mg/mL with the partially purified Protein A peak and the product was recovered in the column effluent during the load cycle and some column volumes of the wash fraction.

These load conditions were in the flow-through (FT) region. The high throughput screen described in Experiment 2.1 provides estimates for the value of the partition coefficient (Kp) under these conditions of pH and chloride concentration. The runs are ranked by the partition coefficients listed in Table 2.2.1. The bound product was determined by measuring the protein in the column strip using UV absorbance. This method of determining the amount of bound product typically underestimates the total amount of product bound due to isocratic elution of product in the wash. Protein A, HCP, HMW and LMW removal results from these experiments are also presented in Table 2.2.1. There is relatively poor and variable removal of HCP, and no removal of Protein A and product variants (HMW and LMW species).

TMAE HiCap (M) Chromatography

The partially purified antibody from a Protein A step run essentially the same as previously described was further purified over the TMAE step under weak partitioning (WP) conditions of pH and chloride content as described below. Column diameters ranged from 0.5 to 3.2 cm and the column heights were 9.4-9.5 cm.

The columns were equilibrated with 5 column volumes of a solution containing 50 mM Tris, 2M NaCl pH 7.5 or 8.0 followed by another equilibration step comprising a 50 mM glycine, 50 mM Tris, pH 7.5 or 8.0 solution. The columns were then loaded to between 124 mg/mL and 303 mg/mL with the partially purified Protein A peak and the product was recovered in the column effluent during the load cycle and some column volumes of the wash fraction. The results from this experiment are presented in Table 2.3.1.

These load conditions are in the weak partitioning (WP) region. The high throughput screen described in Experiment 2.1 provides estimates for the value of the partition coefficient (Kp). The runs are ranked by the partition coefficients listed in Table 2.3.1. The bound product was determined by measuring the protein in the column strip using UV absorbance. This method of determining the amount of bound product typically underestimates the total amount of product bound due to isocratic elution of product in the wash. Protein A, HCP,

TABLE 2.2.1

Removal of HCP, Protein A and HMW and LMW in FT mode

| Kp | Product bound (mg/mL) | pH | Cl- (mM) | Load Challenge (mg/mL) | ProA In load (ppm) | HCP In load (ppm) | HCP (LRV) | ProA (LRV) | HMW (fold) | LMW (fold) | Recovery (%) |
|---|---|---|---|---|---|---|---|---|---|---|---|
| 0.1 | 0.5 | 6.5 | 83 | 150 | ND | 4166 | 1.8 | ND | 1 | 1.1 | >95% |
| 0.2 | 0.8 | 7.0 | 83 | 275 | 25 | 1575 | 0.6 | <0.1 | 1 | 1 | >95% |
| 0.2 | ND | 7.3 | 83 | 109 | 24 | 3117 | 2.4 | <0.1 | 1 | 1 | >95% |
| 0.3 | 0.3 | 7.5 | 83 | 167 | ND | 4572 | 1.8 | ND | 1 | 1 | >95% |

ND = Not determined

Experiment 2.3

Column Runs Under Weak Partitioning Conditions for Mab-IMA

The following column experiments were performed in the weak partitioning mode under conditions identified by the HTS screening (Experiment 2.1). Seven runs were performed over the TMAE column from partially purified Protein A pools.

HMW and LMW results from these experiments are also presented in Table 2.2.1. There is consistent and high removal of HCP, excellent removal of Protein A, and valuable reduction of product variants (HMW and LMW species).

A comparison of the data presented in Tables 2.2.1 and 2.3.1 confirms that the removal of HCP, Protein A, HMW, and LMW under conditions of a flow-through mode (Kp values of ≦0.3) is much lower than what can be achieved under weak partitioning conditions (Kp values >0.3), even when the load challenge exceeds 300 mg/mL.

TABLE 2.3.1

Removal of HCP, Protein A, HMW, and LMW under weak partitioning conditions.

| Kp | Product bound (mg/mL) | pH | Cl- (mM) | Load Challenge (mg/mL) | ProA In load (ppm) | HCP In load (ppm) | HCP (LRV) | ProA (LRV) | HMW (fold) | LMW (fold) | Recovery (%) |
|---|---|---|---|---|---|---|---|---|---|---|---|
| 0.6 | ND | 7.5 | 14 | 303 | 72 | 754 | 1.9 | 1.6 | 1.3 | 1.5 | >95% |
| 0.7 | ND | 8.0 | 55 | 303 | 72 | 754 | 2.0 | 1.5 | 1.0 | 1.2 | >95% |
| 0.7 | 4 | 7.9 | 45 | 307 | 213 | 1852 | 2.6 | 2.4 | ND | ND | >95% |
| 1.0 | 5 | 8.1 | 45 | 302 | 222 | 1852 | 2.6 | 3.0 | ND | ND | >95% |
| 1.2 | 30 | 8.0 | 35 | 124 | 52 | 3320 | 2.8 | >2.1 | 1.4 | 1.1 | 89% |
| 1.7 | ND | 8.0 | 26 | 303 | 72 | 754 | 2.3 | >2.6 | 1.1 | 1.8 | >95% |

TABLE 2.3.1-continued

Removal of HCP, Protein A, HMW, and LMW under weak partitioning conditions.

| Kp | Product bound (mg/mL) | pH | Cl− (mM) | Load Challenge (mg/mL) | ProA In load (ppm) | HCP In load (ppm) | HCP (LRV) | ProA (LRV) | HMW (fold) | LMW (fold) | Recovery (%) |
|---|---|---|---|---|---|---|---|---|---|---|---|
| 1.7 | 9 | 8.1 | 31 | 310 | ND | ND | ND | ND | ND | ND | 90% |
| 1.8 | 25 | 7.8 | 14 | 169 | 23 | 2462 | 3.0 | >1.8 | 1.9 | 2.1 | 86% |
| 5.2 | 9 | 8.0 | 17 | 303 | 72 | 754 | 2.0 | >2.6 | 1.7 | 1.6 | >95% |
| 8.9 | 59 | 8.2 | 12 | 284 | ND | ND | ND | ND | 1.5 | 2.1 | 75% |

ND = not determined

Experiments 2.4

Performance of Weak Partitioning Column Runs at Pilot and Clinical Manufacturing Scale The TMAE process step for the purification of Mab-IMA operated in the weak partitioning zone was scaled-up to the Pilot plant and clinical manufacturing. The culture containing the monoclonal antibody was first purified using a 3L or 5L MabSelect column in Pilot and a 28 L MabSelect column during clinical manufacturing. The MabSelect column was essentially operated as described in Experiment 1.2. The neutralized Protein A peak pools from these runs were further purified on a 1.5 L TMAE column in Pilot and a 7 L TMAE column in the clinical manufacturing facility. The results of three Pilot runs and nine clinical manufacturing runs are summarized in Tables 2.4.1 and 2.4.2, respectively. The step performance was consistent across the runs, with excellent reduction of HCP, Protein A, and good removal of product related HMW and LMW species. Product recovery was >87% in all runs. An estimate of the product bound to the resin during the Pilot runs was obtained from the product in the column strip, which ranged from 6-14 mg/mL of resin.

Summary

HTS identified conditions for WP and FT operation. The FT mode provided only a modest reduction in HCP and LMW species, and no reduction in Protein A residuals or HMW species. Operation in the WP mode improves the removal of all impurities without sacrificing product yield. The process step was scaled up to the Pilot plant and operated consistently for three runs, with very high LRVs for HCP and Protein A, and good reductions in HMW and LMW species.

Series 3—Anion Exchange Using TMAE-HiCapM and Mab-AAB

Experiment 3.1

High Throughput Screen to Establish WP and FT Conditions

Experiment 3.1 was performed using procedures as described in Experiment 1.1.

Experiment 3.2

Column Capacity Runs Under Conditions Corresponding to Varying Partition Coefficients Five chromatography experiments were performed under conditions corresponding to a range of partition coefficients

TABLE 2.4.1

Performance of Pilot Scale runs under Weak Partitioning conditions

| | Kp | Product bound (mg/mL) | pH | Cl− (mM) | Load Challenge (mg/mL) | HCP (LRV) | ProA (LRV) | HMW (fold) | LMW (fold) | Recovery (%) |
|---|---|---|---|---|---|---|---|---|---|---|
| Run 1 | 1.7 | 14 | 8.1 | 31 | 253 | 3.4 | >2.6 | 2.0 | 2.0 | 90 |
| Run 2 | 1.7 | 13 | 8.1 | 31 | 184 | >3.6 | >2.6 | 1.0 | 3.0 | 88 |
| Run 3 | 1.7 | 6 | 8.1 | 31 | 150 | ND | >2.8 | 1.3 | 1.2 | 88 |

ND = not determined

TABLE 2.4.2

Performance of manufacturing scale runs under weak partitioning conditions

| | Kp | Load Challenge (mg/mL) | Cl− (mM) | pH | HCP* (LRV) | ProA* (LRV) | HMW (fold) | LMW (fold) | Recovery (%) |
|---|---|---|---|---|---|---|---|---|---|
| Run 1 | 3.2 | 90 | 30 | 8.1 | >2.2 | ≧0.8 | 2.5 | 3.0 | 90 |
| Run 2 | 2.5 | 180 | 29 | 8.0 | >2.2 | ≧0.0 | 1.9 | 1.5 | 93 |
| Run 3 | 2.6 | 133 | 28 | 8.0 | >2.3 | ≧1.0 | 2.5 | 1.8 | 95 |
| Run 4 | 2.6 | 174 | 29 | 8.0 | >2.2 | ≧1.0 | 2.5 | 1.2 | 94 |
| Run 5 | 2.2 | 136 | 31 | 8.0 | >2.0 | ≧0.9 | 2.3 | 1.7 | 102 |
| Run 6 | 3.8 | 146 | 27 | 8.1 | >2.2 | ≧0.8 | 2.5 | 1.8 | 91 |
| Run 7 | 2.0 | 118 | 28 | 7.9 | >2.2 | ≧1.0 | 1.6 | 1.6 | 96 |

*The HCP and Protein A levels in TMAE peak pool were below limit of quantitation.

identified by HTS screen (Experiment 3.1). The TMAE columns were loaded to a very high load challenge (>1000 g/L) to specifically highlight the superior performance of the AEX step under weak partitioning conditions.

The following conditions were used for the AEX runs performed in Series 3 (exceptions are noted in the individual experimental descriptions).

Operational flow rate—150-300 cm/hr
Equilibration 1—50 mM Tris, 2.0 M NaCl, pH 7.5 (5 column volumes)
Equilibration 2—as specified, approximately equivalent to the load pH and chloride content
Post load wash—as specified, approximately equivalent to the load pH and chloride content
Strip buffer—50 mM Tris, 2.0 M NaCl, pH 7.5 (5 column volumes)

The column was equilibrated with 5 column volumes of equilibration buffer 1 followed by 5 column volumes of equilibration 2 step. The column was then loaded to between 940 and 2144 mg of product/ml of resin with the Protein A peak pool (refer to Series 1, Experiment 1.1) adjusted to the appropriate equilibration 2 buffer.

The column effluent fractions were collected and subsequently assayed for HCP and residual Protein A levels. The load conditions used in these experiments correspond to progressively increasing partition coefficients that span the flow-through and weak partitioning (WP) regions. The high throughput screen described in Experiment 3.1 provided estimates for the value of the partition coefficient (Kp). The bound product values in this example were calculated based on the product eluted in the strip. The results from these experiments are presented in Table 3.2.1 and FIGS. 10A and 10B.

TABLE 3.2.1

Summary of results from very high load challenge experiments in the WP mode

| | Partition Coefficient Kp | Operating conditions | Load Challenge mg/ml | Product bound mg/mL* | Recovery* |
|---|---|---|---|---|---|
| Run 1 | 0.1 | Flow-through | 1754 | 0 | 100 |
| Run 2 | 0.23 | Weak Partitioning | 940 | 14.2 | 98.5 |
| Run 3 | 0.8 | Weak Partitioning | 940 | 12.0 | 98.7 |
| Run 4 | 0.8 | Weak Partitioning | 2144 | 23.0 | 98.9 |
| Run 5 | 2.73 | Weak Partitioning | 960 | 12.6 | 98.7 |
| Run 6 | 7 | Weak Partitioning | 1130 | 71.7 | 93.7 |

*Based on mass balance calculations.

The product bound value for the run corresponding to a Kp of 0.1 was near zero, as is expected for a typical flow-through operation. The product bound values for experiments performed in the weak partitioning region were >12.0 mg/ml in all cases. In fact, the product bound value for the run corresponding to the Kp of 7 was as high as 71 mg/ml. The product recovery in the combined load eluate and wash fractions in all cases were, however, >93%.

HCP and Protein A removal, as a function of load challenge, is presented in FIGS. 10A and 10B. As discussed earlier, the HCP removal increases significantly as conditions move from flow-through to weak partitioning. Operating under flow-through conditions provides approximately 1.5 logs of HCP clearance, while the HCP log removal values were as high as 3.8 logs at load challenges <450 mg/ml of resin when operated at a Kp of 7 in the weak partitioning region. At a Kp of 0.8 in the weak partitioning region, 2.8 logs of HCP clearance was obtained for load challenges up to 1000 mg/ml of the resin, and >3 logs of HCP clearance was obtained for up to a load challenge of 800 mg/ml of resin at a Kp of 2.7 in the weak partitioning region.

As in the case of HCP, Protein A removal increases significantly as we move from flow-through conditions to weak partitioning conditions. The results presented in FIGS. 10A and 10B also highlight the fact that increasing the Kp of operation from the flow-through to weak partitioning region increases both the HCP and Protein A log clearance values obtained prior to breakthrough of the contaminant, as well as the load challenge corresponding to the point of breakthrough. A further increase in Kp continues to increase the HCP and Protein A LRV prior to breakthrough of the contaminant. However, the point of breakthrough occurs at relatively lower load challenges as the bound product now competes with the contaminants for the binding sites. Nevertheless, the column capacity for the runs presented here were very high even for the high Kp run.

Summary

In this example it was shown that Protein A and HCP removal can be significantly improved by operating the AEX step under weak partitioning conditions and at load challenges in excess of 1000 mg/ml of resin. This example highlights one fundamental difference between weak partitioning chromatography and the standard operations under binding conditions. The weak partitioning conditions push the limits of product binding only up to a point where the contaminant clearance is significantly improved, while product recovery and load challenges remain high. The Kp values corresponding to binding conditions are >20 in AEX; under these conditions the competitive effects between product and contaminant are very strong leading to reduced capacity as compared to weak partitioning chromatography.

Series 4—Hydrophobic Interaction using Phenyl Toyopearl and Mab-AAB

Experiment 4.1

Batch Binding Studies to Establish WP and FT Conditions

Batch binding studies were conducted to identify the weak partitioning and flow-through conditions for Mab-AAB with Phenyl Toyopearl medium from Tosoh Biosciences. The salt modulating the strength of the product interaction with the resin is $Na_2SO_4$, which was varied from 0.20 to 0.90M. The solutions were buffered to control at pH 7.5. 45 um filter plates were used to incubate the resin with liquid and to decant the supernatant through centrifugation. Eight Tris/$Na_2SO_4$ buffers were made with $Na_2SO_4$ at different concentrations (0.2 M to 0.9 M). Mab-AAB which was partially purified by Protein A chromatography was diluted into Tris/$Na_2SO_4$ solution to a final of concentration of 0.87 mg/ml. 50 ul of resin was equilibrated with 300 ul of buffer and then the supernatant decanted for each of the Tris/$Na_2SO_4$ conditions; this equilibration was repeated three times. After equilibration, decanted resin was mixed with product at the same salt concentration and pH and incubated for 30 minutes with gentle shaking. The load challenge was 5.2 mg product/ml of resin for all conditions. A UV plate was then stacked at the bottom of the filter plate to collect the supernatant upon centrifugation. Subsequently, 300 ul of 50 mM Tris, pH 7.5 buffer was applied to the resin to strip off bound product. Following a 20 minute incubation, the strip was collected in a separate UV plate through centrifugation. The concentration of the product in each fraction was measured by UV absorbance and the extinction coefficient for this MAb. The calculations were adjusted for a stage-to-stage carry over volume of 29 ul that was determined through a separate set of experiments. The experiment was repeated four times under each salt condition and an average partition coefficient is reported.

Table 4.2.1 summarizes the partition coefficients from this experiment. The highest concentrations of $Na_2SO_4$ caused strong product binding, while salt concentrations in the range of 0.40-0.55M represent weak partitioning conditions.

Experiment 4.2

Column Runs Under Weak Partitioning, Flow-through and Binding Conditions (High Product Challenge Studies)

Column runs were performed under flow-through, weak partitioning and strong binding conditions. For all Phenyl Toyopearl hydrophobic interaction chromatography runs described in the Series 4 experiments, the following conditions were used (exceptions are noted in the individual experimental descriptions).

Column dimension: diameter 0.5 cm, bed height 9.5-10.5 cm and appropriate $[Na_2SO_4]$ at specified concentration. The Protein A peak was first concentrated 10-fold, and subsequently diluted to 14.77 mg/ml in the appropriate salt concentration. Host cell protein (HCP) and residual Protein A levels in the load material were 30911 ppm and 17.1 ppm, respectively. All column runs were performed at a load challenge of 100 mg/ml of resin. The product was collected in the column effluent during the load cycle fraction. After product flow-through, ten column volumes of wash buffer at the same salt concentration as load were applied to the column, followed by five column volumes of a strip buffer containing 50 mM Tris, pH 7.5. HCP and Protein A content in the load eluate and wash samples were subsequently analyzed by ELISA. The combined impurity level in both load eluate and wash fractions is reported in Table 4.2.1.

The runs are ranked by the partition coefficients. The bound product was determined by measuring the protein in the column strip using UV absorbance. This method of determining the bound product typically underestimates the amount of product bound during the load due to the gradual desorption of the product during the wash.

TABLE 4.2.1

Impurity removal in flow-through, weak partitioning and strong binding conditions

|  | Na2SO4 Conc | Partition Coefficient Kp | Operating window | Bound Product (mg/mL) | Product Recovery (%) | Protein A removal (fold) | HCP removal (Log) |
|---|---|---|---|---|---|---|---|
| Run 1 | 0.10 M | <0.1 | Flow-Through | 0.6 | 94 | 0.9 | 0.3 |
| Run 2 | 0.20 M | <0.1 | Flow-Through | 1.3 | 93 | 0.8 | 0.4 |
| Run 3 | 0.40 M | 0.9 | Weak Partitioning | 2.8 | 94 | 1.7 | 1.0 |
| Run 4 | 0.45 M | 2.0 | Weak Partitioning | 3.0 | 93 | 1.5 | 0.9 |
| Run 5 | 0.50 M | 4.3 | Weak Partitioning | 3.8 | 92 | 2.5 | N/A |
| Run 6 | 0.55 M | 9.9 | Weak Partitioning | 5.0 | 93 | 3.4 | 1.1 |
| Run 7 | 0.80 M | >100 | Strong Binding | 25 | 72 | 2.2 | 0.7 |
| Run 8 | 0.90 M | >100 | Strong Binding | 34 | 67 | 1.1 | 0.4 |

(The partition coefficient Kp accounts for the phase volume ratio of 6 from 50 microliters of resin and 300 microliters of solution.)

Equilibration—50 mM Tris, pH 7.5 with $[Na_2SO_4]$ approximately equivalent to the load
Load—$[Na_2SO_4]$ as specified below
Wash—$[Na_2SO_4]$ equal to the load (exceptions noted below)
Strip—50 mM Tris, pH 7.5

Two different loads were used: i) partially purified antibody pools from a Protein A step run essentially the same as those previously described or ii) more pure TMAE Q Sepharose FF product pools from FT mode operation.

Experiment 4.2.1

Column Runs Using Protein A Peak Pool as Load

The experiments discussed here were performed to highlight the superior performance of HIC under weak partitioning conditions. Column runs were performed under varying salt concentrations to cover a range of partition coefficients that correspond to flow-through, weak partitioning and strong binding conditions. The batch binding screen described in Experiment 4.1 provides estimates for the value of the partition coefficient (Kp). The columns were equilibrated with 5 column volumes of a solution containing 50 mM Tris, pH 7.5

As is evident from the data presented in Table 4.2.1, the performance of the HIC step improves significantly with respect to contaminant reduction as we move from flow-through conditions to weak partitioning conditions, while product recovery is comparable. A further increase in the operating salt concentration leads to partition coefficients that correspond to the strong binding conditions. It is once again clear from the data presented in Table 4.2.1 that the HIC step performance deteriorates with respect to both contaminant reduction, as well as product recovery, as we move from weak partitioning to strong binding conditions. The optimum operating window for this separation therefore corresponds to that of weak partitioning chromatography. Under weak partitioning conditions, the HIC step provides 1 log reduction of HCP and a 3.4 fold reduction of Protein A. The bound product levels under the weak partitioning conditions, in this example, were between 2.8-5 mg/ml of the resin.

Experiment 4.2.2

Column runs Using Q-Sepharose Peak Pool as Load

The Q Sepharose FF peak pool was used in these sets of experiments to highlight the fact that the performance of the HIC step under the optimum weak partitioning chromatography conditions can be further improved with a cleaner feedstock. The load material in this case contained 2880 ppm of HCP and was generated by purifying the Protein A peak pool on a Q-Sepharose FF column. Two experiments, one under weak partitioning conditions and the other under typical flow-through conditions, were conducted to compare the column performance with respect to impurity removal. The Q-Sepharose peak was diluted to 3.27 mg/ml at 550 mM $Na_2SO_4$ and loaded to the column to a load challenge of 100 mg/ml of resin for operation under weak partitioning conditions. The column was subsequently washed with 10 CVs of a buffer containing the same salt concentration as the load and stripped with 6CV of 50 mM Tris buffer, pH 7.5. The second experiment was conducted under flow-through conditions. The load was adjusted to 3.03 mg/ml in 200 $Na_2SO_4$ and loaded to the column to a load challenge of 90 mg/ml of resin. The column was then washed with 6CV of a buffer containing the same salt concentration as the load, and subsequently stripped with 6 CV of 50 mM Tris buffer, pH 7.5. In both runs, the flow-through and wash fractions were collected for recovery and impurity analysis. The results from these runs are reported in Table 4.2.2.

TABLE 4.2.2

Comparison of HIC weak partitioning results to flow-through results

| Run | $Na_2SO_4$ Conc | Partition Coefficient (Kp) | Operating mode | Load Challenge (mg/mL) | Bound Product (mg/mL) | Product Recovery | HCP LRV |
| --- | --- | --- | --- | --- | --- | --- | --- |
| 1 | 0.55 M | 9.9 | Weak Partitioning | 100 | 3.0 | 94% | >2 |
| 2 | 0.20 M | <0.1 | Flow-through | 90 | 0.1 | 99% | <0.5 |

The product recovery values under weak partitioning conditions were comparable to flow-through operations and were also independent of the feedstock used in these experiments. The performance of the steps with respect to HCP removal is significantly higher under weak partitioning conditions as compared to flow-through operation.

HCP LRV across the HIC step with either feedstock was comparable under flow-through conditions (~0.4-0.5 LRV). However, the HCP LRV values for experiments performed under weak partitioning conditions increased from 1 LRV with the Protein A load material to greater than 2 LRV with load material purified through Protein A and Q Sepharose FF columns.

Summary

Another mode of chromatography (HIC) was shown to operate successfully in a weak partitioning mode. The performance of the HIC step under weak partitioning conditions was shown to be superior to both flow-through conditions, as well as to operations under tighter binding conditions, with respect to product recovery and HCP/Protein A removal. A high load challenge capacity of 100 mg/ml of resin was successfully processed under weak partitioning conditions, where >3 mg/mL of product bound to the resin (even though the load concentration was 3.27 mg/mL). The partition coefficients corresponding to optimum weak partitioning conditions appear to be slightly higher than those for anion exchange chromatography.

Series 5—Hydroxyapatite using Ceramic Hydroxyapatite Type I and Mab-MYA

Experiment 5.1

High Throughput Screen to Establish WP and FT Conditions

A high throughput screen (HTS) was performed to identify the weak partitioning and flow-through conditions for Mab-MYA with ceramic hydroxyapatite medium. This screen varied the concentration of sodium chloride and sodium phosphate to determine their effect on the extent of binding of MAB-MYA to the hydroxyapatite medium.

50 μL of ceramic hydroxyapatite medium was added to 30 wells of a 96 well filter plate. Each well was equilibrated in solutions made up of the appropriate sodium chloride and sodium phosphate concentrations in a 100 mM HEPES buffer containing 100 mM arginine at pH 7.2. The concentrations of the two salts in the solution are shown in Tables 5.1.1 and 5.1.2. Each condition was performed in duplicate. The MAB-MYA load challenge in each of these wells was of 5.0 mg/mL of resin

TABLE 5.1.1

Sodium chloride levels in each well (in mM)

|   | 1 | 2 | 3 | 4 |
| --- | --- | --- | --- | --- |
| A | 50 | 200 | 50 | 200 |
| B | 750 | 50 | 750 | 50 |
| C | 50 | 380 | 50 | 380 |
| D | 500 | 760 | 500 | 760 |
| E | 50 | 1140 | 50 | 1140 |
| F | 200 | 200 | 200 | 200 |
| G | 350 | 200 | 350 | 200 |
| H | 700 |  | 700 |  |

TABLE 5.1.2

Sodium phosphate levels in each well (in mM)

|   | 1 | 2 | 3 | 4 |
| --- | --- | --- | --- | --- |
| A | 5 | 20 | 5 | 20 |
| B | 5 | 30 | 5 | 30 |
| C | 8 | 30 | 8 | 30 |
| D | 8 | 30 | 8 | 30 |
| E | 10 | 30 | 10 | 30 |
| F | 10 | 50 | 10 | 50 |
| G | 10 | 100 | 10 | 100 |
| H | 10 |  | 10 |  |

In the first stage of the HTS experiment, each well was equilibrated in the conditions of sodium chloride and sodium phosphate as described in Tables 5.1.1 and 5.1.2, in a phase volume ratio of 6:1 (300 uL solution: 50 uL resin). The plate was shaken for 20 minutes, allowing equilibrium to be reached. The solution was then removed by centrifuging the filter plate. This equilibration cycle was repeated three times.

In the second stage, the resin in each well was challenged with a concentrated MAb-MYA solution to the appropriate protein load challenge with a volume ratio of 6:1 (300 uL solution: 50 uL resin) at the appropriate sodium chloride and sodium phosphate concentration. A 7.0 mg/mL solution of Mab-MYA in 50 mM NaCl, 100 mM HEPES, 100 mM arginine, pH 7.2 was used as stock solution. The loaded plate was shaken for 20 minutes, allowing the resin and solution to equilibriate. The supernatant was removed from the filter plate by centrifugation and collected into a collection plate. The protein concentration in the supernatant in each well was determined by absorbance at A280 nm.

In the third stage, resin was washed by adding solutions of the specified sodium chloride and sodium phosphate conditions listed in Tables 5.1.1 and 5.1.2. The supernatant was removed after shaking for 20 minutes.

In the fourth stage, a buffer comprised of 100 mM sodium phosphate, 1M NaCl pH 7.2 was added to remove the remaining protein that was bound to the resin.

The partition coefficients were calculated for each well using the mass eluted from stage 4 and the product concentration from stage 2, and are shown in Table 5.1.3.

TABLE 5.1.3

Partition Coefficients (Kp) for the 96 well HTS screen for MAB-MYO

|   | 1 | 2 | 3 | 4 |
|---|---|---|---|---|
| A | 49.3 | 2.3 | 50.5 | 2.4 |
| B | 3.5 | 6.0 | 4.1 | 6.0 |
| C | 31.6 | 0.4 | 34.7 | 0.3 |
| D | 2.9 | 0.1 | 3.3 | 0.1 |
| E | 28.1 | 0.0 | 28.3 | 0.0 |
| F | 7.2 | 0.5 | 7.7 | 0.4 |
| G | 3.5 | 0.0 | 3.1 | 0.0 |
| H | 1.1 |  | 1.1 |  |

As shown in Table 5.1.3, the Kp value can be used to describe regions where MAB-MYA binds to the hydroxyapatite medium with different strengths. The strength of MAB-MYA binding to ceramic hydroxyapatite medium can be manipulated by varying conditions of chloride and phosphate concentration into flow-through (Kp=<0.1), weak partitioning (0.1<Kp<20), and binding zones (Kp=>20).

Experiment 5.2

Column Runs Under WP Conditions

The experiments discussed here were specifically performed to highlight the superior performance of the cHA step under weak partitioning conditions. The experiments were therefore performed under conditions corresponding to a range of partitioning coefficients identified by the HTS screen (Experiment 5.1). Twelve runs were conducted, with product load challenges of 100 mg/ml of resin.

Mabselect Protein A Chromatography

The culture containing the monoclonal antibody was purified using a MabSelect column. A Mabselect Protein A column was equilibrated with 5 column volumes of 50 mM Tris/150 mM NaCl, pH 7.5 at a flow rate of 300 cm/hr. The column was then loaded at a load of approximately 40 mg product/ml resin. This was followed by a 10CV wash in 1M arginine, 50 mM Tris, pH 7.5 and a 5CV wash containing 10 mM Tris, 75 mM NaCl, pH 7.5 wash. The column was then eluted using 100 mM arginine, 50 mM NaCl, pH 3.0. The product pool was neutralized to pH 7.2 using 2M HEPES pH 8.0.

Ceramic Hydroxyapatite Chromatography

The partially purified antibody pools from the Protein A step were further purified over hydroxyapatite. The column diameter was 0.5 cm and the column height was 10 cm.

For all hydroxyapatite chromatography steps described in the Experiment 5 series, the following conditions were used (exceptions are noted in the individual experimental descriptions).

Operational flow rate—150-240 cm/hr

Equilibration 1 300 mM sodium phosphate, 1.0M NaCl, pH 6.8 (3 column volumes)

Equilibration 2 5-30 mM sodium phosphate, 50-760 mM NaCl, 100 mM Arg, 100 mM HEPES pH 7.2 (5 column volumes)

Wash 5-30 mM sodium phosphate, 50-760 mM NaCl, 100 mM Arg, 100 mM HEPES pH 7.2 (5-10 column volumes)

The column was equilibrated with 5 column volumes of equilibration buffer 1 followed by another equilibration 2 step. The column was then loaded to 100 mg product/ml resin with the Protein A peak from the previous step (adjusted to the appropriate equilibration 2 buffer), and the product was recovered in the column effluent during the load cycle and some column volumes of the wash fraction. The results from these experiments are presented in Table 5.2.1 and FIG. 11.

These load conditions were in the flow-through, weak partitioning (WP) and binding regions. The high throughput screen described in Experiment 5.1 provides estimates for the value of the partition coefficient (Kp) and the bound product (mg/mL of resin) under these conditions of chloride and phosphate concentration. The bound product was determined from the product breakthrough volumes from the column runs. HCP and Protein A results from these experiments are presented in Table 5.2.1 and FIG. 11.

TABLE 5.2.1

Removal of HCP and Protein A under flow-through, weak partitioning and binding conditions

|  | Partition Coefficient Kp | Operating Mode | Phos | NaCl | Bound Product (mg/mL) | Product Recovery (%) | Protein A removal (fold) | Host Cell Protein (LRV) |
|---|---|---|---|---|---|---|---|---|
| Run 1 | 0.0 | Flow-through | 30 | 760 | 0 | 93 | 0 | 0.58 |
| Run 2 | 0.9 | Weak Partitioning | 30 | 200 | 3.0 | 96 | NA | 0.57 |
| Run 3 | 1.1 | Weak Partitioning | 10 | 700 | 3.2 | 94 | 1.7 | 0.9 |
| Run 4 | 1.7 | Weak Partitioning | 20 | 200 | 3.1 | 94 | NA | 0.83 |
| Run 5 | 3.0 | Weak Partitioning | 8 | 500 | 3.0 | 100 | 1.9 | 1.3 |

TABLE 5.2.1-continued

Removal of HCP and Protein A under flow-through, weak partitioning and binding conditions

|  | Partition Coefficient Kp | Operating Mode | Phos | NaCl | Bound Product (mg/mL) | Product Recovery (%) | Protein A removal (fold) | Host Cell Protein (LRV) |
|---|---|---|---|---|---|---|---|---|
| Run 6 | 3.2 | Weak Partitioning | 10 | 350 | 3.6 | 94 | 2.1 | 1.5 |
| Run 7 | 3.7 | Weak Partitioning | 5 | 750 | 3.3 | 99 | 2.4 | 1.2 |
| Run 8 | 5.8 | Weak Partitioning | 30 | 50 | 10.7 | 95 | 2.1 | 1.2 |
| Run 9 | 7.3 | Weak Partitioning | 10 | 200 | 10.2 | 94 | 2.4 | 1.2 |
| Run 10 | 27.8 | Strong Binding | 10 | 50 | 16.3 | 91 | 2.1 | 1.2 |
| Run 11 | 32.7 | Strong Binding | 8 | 50 | 21.6 | 86 | 2.4 | 1.4 |
| Run 12 | 49.2 | Strong Binding | 5 | 50 | 24.6 | 79 | 2.1 | 1.6 |

Figure 11:
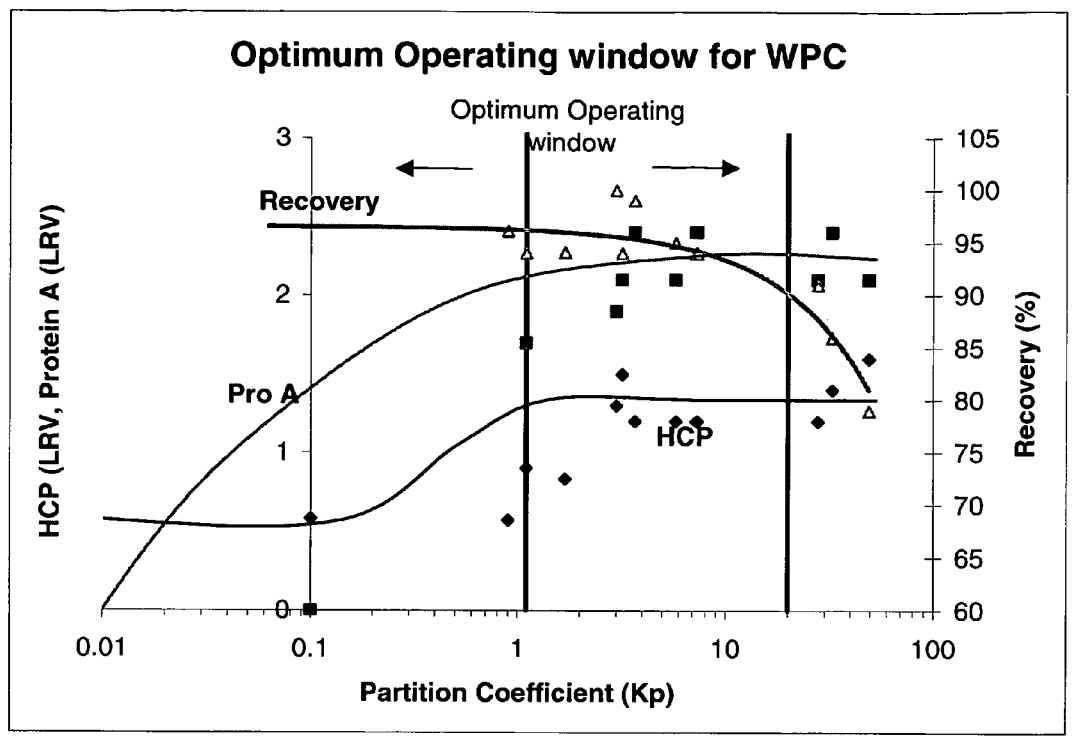
FIG. 11 shows for Mab-MYA, the optimum operating window for weak partitioning chromatography in hydroxyapatite. The optimum Kp in this example is between 1.5 and 20.

It is evident from the data presented in Table 5.2.1 and FIG. 11 that the performance of the cHA step improves significantly with respect to contaminant reduction as we move from flow-through conditions to weak partitioning conditions, while product recovery is comparable. Operating under conditions corresponding to a further increase in the partition coefficient (i.e., operating in the binding region) provides no additional benefit with respect to contaminant removal. However, product recovery across the step begins to drop under strong binding conditions. Thus, the optimum operating window for this separation corresponds to that of weak partitioning chromatography. Under these conditions, >2 log reduction of Protein A and >1.2 log reduction of host cell protein was obtained at a load challenge of 100 mg of product/ml of resin. Bound product levels under the weak partitioning conditions, in this example, were between 3.0-10.2 mg/mL of the resin.

Summary

A third mode of chromatography (hydroxyapatite) was shown to operate successfully in a weak partitioning mode. Protein A and HCP bind more tightly than the product antibody to ceramic resin, and are retained strongly under WP conditions. Higher values of Kp in the WP region are between 10 and 20 in some cases, which still provide good product recovery (>90%). Lower levels of Kp give correspondingly higher recoveries.

In this example it was shown that the performance of the column step can be optimized primarily through the choice of partition coefficient used to run the column. The partition coefficient in hydroxyapatite is a complex function of pH, salt (type and concentration), phosphate, and buffer components. All of these variables in general have an impact on the performance of the column step. The approach presented here provides a simple means of relating the impact of changing any one of these variables on column performance. The unified 'partition coefficient' approach presented in this example opens up the possibility of operating in a wider operating space in this mode of chromatography than has been done before. The weak partitioning conditions for optimum performance can easily be identified using the HTS methods described above.

Series 6—Hydroxyapatite Using Ceramic Hydroxyapatite Type I and Mab-A5T

Experiment 6.1

High Throughput Screen to Establish WP and FT Conditions

A high throughput screen (HTS) was performed to identify the weak partitioning and flow-through conditions for Mab-A5T with ceramic hydroxyapatite medium. This screen varied pH, sodium chloride and sodium phosphate concentrations to determine their effect on the extent of binding of MAB-A5T to the hydroxyapatite medium.

50 µL of ceramic hydroxyapatite medium was added to 36 wells of a 96 well filter plate. Each well was equilibrated in solutions made up of the appropriate sodium chloride and sodium phosphate concentrations in a 50 mM HEPES buffer containing 50 mM arginine at either pH 7.0 or pH 8.0. The concentrations of the two salts in the solution are shown in Tables 6.1.1 and 6.1.2. The conditions shown in columns 1-3 were performed at pH 7.0, and columns 4-6 were performed at pH 8.0. The MAB-A5T load challenge in each of these wells was of 5.0 mg/mL of resin.

TABLE 6.1.1

Sodium chloride levels in each well (in mM)

|  | 1 | 2 | 3 | 4 | 5 | 6 |
|---|---|---|---|---|---|---|
|  | pH 7.0 | | | pH 8.0 | | |
| A | 50 | 400 | 400 | 50 | 400 | 400 |
| B | 50 | 50 | 400 | 50 | 50 | 400 |
| C | 50 | 50 |  | 50 | 50 |  |
| D | 100 | 50 |  | 100 | 50 |  |
| E | 100 | 100 |  | 100 | 100 |  |
| F | 100 | 100 |  | 100 | 100 |  |
| G | 400 | 100 |  | 400 | 100 |  |
| H | 400 | 400 |  | 400 | 400 |  |

TABLE 6.1.2

Sodium phosphate levels in each well (in mM)

|  | 1 | 2 | 3 | 4 | 5 | 6 |
|---|---|---|---|---|---|---|
|  | pH 7.0 | | | pH 8.0 | | |
| A | 2 | 32 | 8 | 2 | 32 | 8 |
| B | 8 | 2 | 32 | 8 | 2 | 32 |
| C | 32 | 8 |  | 32 | 8 |  |
| D | 2 | 32 |  | 2 | 32 |  |
| E | 8 | 2 |  | 8 | 2 |  |
| F | 32 | 8 |  | 32 | 8 |  |
| G | 2 | 32 |  | 2 | 32 |  |
| H | 8 | 2 |  | 8 | 2 |  |

In the first stage of the HTS experiment, each well was equilibrated in the conditions of sodium chloride, sodium phosphate and pH as described in Tables 6.1.1 and 6.1.2 in a phase volume ratio of 6:1 (300 uL solution: 50 uL resin). The plate was shaken for 20 minutes, allowing equilibrium to be reached. The solution was then removed by centrifuging the filter plate. This equilibration cycle was repeated three times.

In the second stage, the resin in each well was challenged with a concentrated MAb-A5T solution to the appropriate protein load challenge with a volume ratio of 6:1 (300 uL solution: 50 uL resin) at the appropriate pH and sodium chloride and sodium phosphate concentration. A 6.9 mg/mL solution of Mab-A5T in 1 mM HEPES, 100 mM NaCl, pH 7.0 was used as stock solution. The loaded plate was shaken for 20 minutes, allowing the resin and solution to equilibrate. The supernatant was removed from the filter plate by centrifugation and collected into a collection plate. The protein concentration in the supernatant in each well was determined by absorbance at A280 nm.

In the third stage, resin was washed by adding solutions of the specified sodium chloride, sodium phosphate and pH conditions listed in Tables 6.1.1 and 6.1.2. The supernatant was removed after shaking for 20 minutes.

In the fourth stage, a buffer comprising 100 mM sodium phosphate, 1M NaCl pH 7.2 was added to remove the remaining protein that was bound to the resin. The partition coefficients were calculated for each well using the mass eluted from stage 4 and the product concentration from stage 2, and are shown in Table 6.1.3.

TABLE 6.1.3

Partition Coefficients (Kp) for the HTS screen for MAB-A5T

|   | 1 | 2 | 3 | 4 | 5 | 6 |
|---|---|---|---|---|---|---|
|   |   | pH 7.0 |   |   | pH 8.0 |   |
| A | 142.7 | 0.1 | 1.6 | 50.2 | 0.0 | 0.3 |
| B | 90.6 | 144.3 | 0.1 | 9.9 | 44.7 | 0.0 |
| C | 12.1 | 84.5 |   | 1.0 | 13.7 |   |
| D | 90.5 | 10.4 |   | 22.2 | 1.1 |   |
| E | 27.5 | 94.1 |   | 4.3 | 21.9 |   |
| F | 2.5 | 28.0 |   | 0.3 | 4.3 |   |
| G | 15.1 | 2.1 |   | 2.2 | 0.4 |   |
| H | 1.2 | 15.1 |   | 0.4 | 2.0 |   |

As shown in Table 6.1.3, the Kp value can be used to identify regions where MAB-A5T binds to the hydroxyapatite medium with different strengths. The strength of MAB-A5T binding to ceramic hydroxyapatite medium can be manipulated by varying conditions of NaCl, phosphate and pH into flow-through, weak partitioning, and binding zones.

Experiment 6.2

Column Runs Under WP Conditions

Experiments were performed to highlight the superior performance of the cHA step under weak partitioning conditions. The experiments were therefore performed under conditions corresponding to a range of partitioning coefficients identified by the HTS screen (Experiment 6.1). Eight runs were conducted, with product load challenges of 110 mg/ml of resin.

Mabselect Protein A Chromatography

The culture containing the monoclonal antibody was purified using a MabSelect column. A Mabselect Protein A column was equilibrated with 5 column volumes of 50 mM Tris/150 mM NaCl, pH 7.5 at a flow rate of 300 cm/hr. The column was then loaded at a load challenge of approximately 40 mg product/ml resin. This was followed by a 5CV wash in 1M NaCl, 50 mM Tris, pH 7.5 and a 5CV wash containing 10 mM Tris, 75 mM Nacl, pH 7.5 wash. The column was then eluted using 100 mM arginine, 50 mM NaCl, pH 3.0. The product pool was neutralized to pH 7.2 using 2M HEPES pH 8.0.

Ceramic Hydroxyapatite Chromatography

The partially purified antibody pools from the Protein A step were further purified over hydroxyapatite. The column diameter was 0.5 cm and the column height was 10 cm. For all hydroxyapatite chromatography steps described in the Experiment 6 series, the following conditions were used (exceptions are noted in the individual experimental descriptions).

Operational flow rate—150-240 cm/hr
Equilibration 1 300 mM sodium phosphate, 1.0M NaCl, pH 6.8 (3 column volumes)
Equilibration 2 2-32 mM sodium phosphate, 50-400 mM NaCl, 5 mM Imidazole, 50 mM glycine, 10 mM HEPES, pH 7.0 (5 column volumes)
Wash Same as Equilibration 2.

The column was equilibrated with 5 column volumes of equilibration buffer 1 followed by another equilibration 2 step. The column was then loaded to 110 mg product/ml resin with the Protein A peak from the previous step (adjusted to the appropriate equilibration 2 buffer), and the product was recovered in the column effluent during the load cycle and some column volumes of the wash fraction. The results from these experiments are presented in Table 6.2.1 and FIG. 12.

TABLE 6.2.1

Partition coefficients for MAB-A5T on cHA resin and the corresponding operating window.

|  | Partition Coefficient Kp | Product Bound mg/ml | Operating mode | Phos mM | NaCl mM | pH |
|---|---|---|---|---|---|---|
| Run 1 | 0.1 | 0 | Flow-Through | 32 | 400 | 7.0 |
| Run 2 | 0.7 | 1.6 | Weak Partitioning | 32 | 170 | 7.0 |
| Run 3 | 1.4 | 2.2 | Weak Partitioning | 32 | 120 | 7.0 |
| Run 4 | 2.1 | 1.6 | Weak Partitioning | 2 | 400 | 7.0 |
| Run 5 | 13.7 | 7.0 | Weak Partitioning | 8 | 50 | 8.0 |
| Run 6 | 22 | 6.7 | Weak Partitioning | 2 | 100 | 8.0 |
| Run 7 | 54 | 12.8 | Strong Binding | 2 | 60 | 8.0 |
| Run 8 | >100 | 16 | Strong Binding | 2 | 50 | 7.0 |

The operating conditions in these experiments correspond to the flow-through, weak partitioning (WP) region and binding regions. The HTS experiment described in Experiment 6.1 provides estimates for the value of the partition coefficient (Kp) under these conditions of pH, chloride and phosphate concentrations. The runs in Table 6.2.1 are ranked by the partition coefficients. The bound product was determined by measuring the protein in the column strip using UV absorbance. This method of determining the bound product typically underestimates the amount of product bound during the load due to the gradual desorption of the product during the wash. HCP and product related HMW removal, as well as product recovery results from these experiments are presented in FIG. 12.

Figure 12:
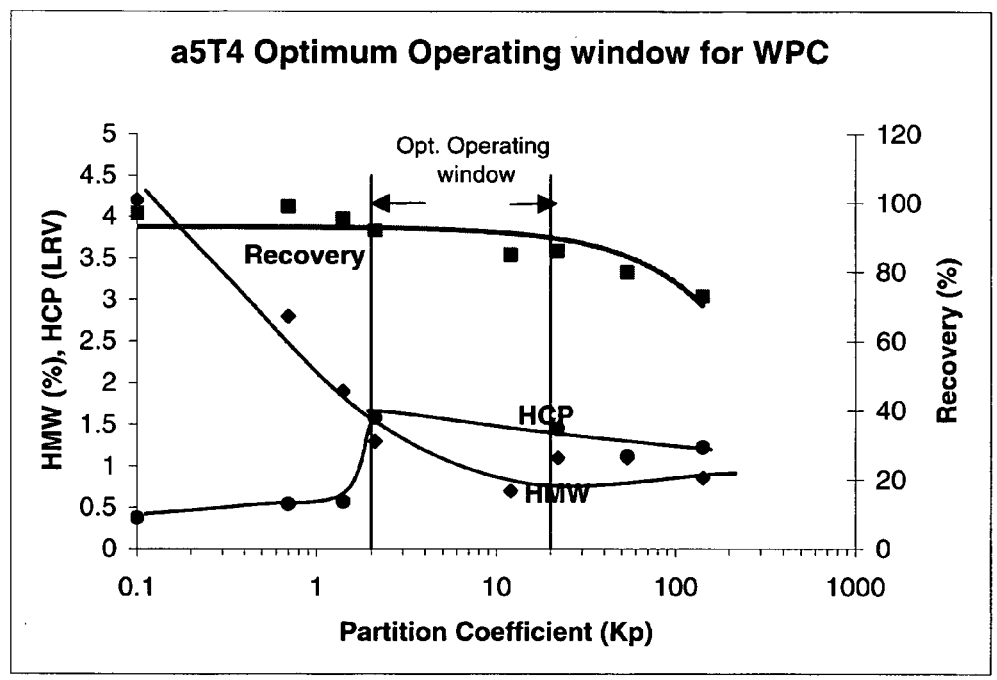
FIG. 12 shows for Mab-A5T4, the optimum operating window for weak partitioning chromatography in hydroxyapatite. The optimum Kp in this example is between 2 and 20.

It is clear from the data presented in FIG. 12 that the performance of the cHA step improves significantly with respect to HCP and HMW reduction as we move from the flow-through conditions to the weak partitioning conditions, while product recovery is maintained at >80%. Operating under conditions corresponding to a further increase in the partition coefficient (i.e., operating in the binding region) provides no additional benefit with respect to contaminant removal. However, the product recovery across the step begins to drop under strong binding conditions. Thus, the optimum operating window for this separation corresponds to that of weak partitioning chromatography. Under these conditions, a 4-fold reduction of product related HMW species and >1.4 log reduction of HCP was obtained at a load challenge of 110 mg of product/ml of resin. The bound product levels under weak partitioning conditions, in this example, were between 1.6-6.7 mg/ml of the resin.

Summary

A second example was presented in hydroxyapatite where operating under weak partitioning chromatography was shown to provide improved performance with respect to HCP and HMW reduction and product recovery (>80%). As in previous examples, the performance of the step was optimized primarily through the choice of partition coefficients used to run the column. The approach presented here provides a simple means of relating the impact of changing any one of several variables (pH, salt, phosphate, imidazole, glycine, HEPES, etc.,) to column performance. The weak partitioning conditions for optimum performance can easily be identified using the HTS methods described in this example. The approach presented here opens up the possibility of operating in a wider operating space in this mode of chromatography than has been done before. The optimal WP region in this example corresponds to partition coefficients between 2 and 20.

Series 7—Hydroxyapatite using Ceramic Hydroxyapatite Type I and Mab-MYO

Experiment 7.1

High Throughput Screen to Establish FT, WP and Strong Binding Conditions

A high throughput screen (HTS) was performed to identify flow-through, weak partitioning and binding conditions for Mab-MYO with ceramic hydroxyapatite medium. This screen varied the concentration of pH, arginine/glycine, HEPES, sodium phosphate and sodium chloride to determine their effect on the extent of binding of MAB-MYO to the hydroxyapatite medium.

The HTS procedures used in this example were similar those described in Series 5 and Series 6 and are not discussed here. Predicted Kp values derived from a response surface fit to the HTS data were used to pick specific conditions for column experiments.

Experiment 7.2

Column Runs Under WP Conditions

The experiments discussed here were performed under conditions corresponding to a range of partitioning coefficients identified by the HTS experiments. These experiments were specifically performed to highlight the superior performance of the cHA step under weak partitioning conditions for the removal of HCP and product related HMW species. Four runs were conducted with a product load challenges of 55 mg/ml of resin. The load challenge used in these experiments is low for weak partitioning chromatography, but is typical for flow-through operation. No attempt was made in these experiments to optimize load challenge for weak partitioning chromatography.

The partially purified antibody pools from the Protein A step were used in these experiments. The column diameter was 0.5 cm and the column height was 10 cm.

For all hydroxyapatite chromatography steps described in the Experiment 7 series, the following conditions were used (exceptions are noted in the individual experimental descriptions).

Operational flow rate—150-240 cm/hr

Equilibration 1 300 mM sodium phosphate, 1.0M NaCl, pH 6.8 (2-5 column volumes)

Equilibration 2 1-8 mM sodium phosphate, 50-1750 mM NaCl, 12-50 mM Arg, 20-50 mM HEPES pH 7.0 (5 column volumes)

Wash Same as Equilibration 2

The column was equilibrated with 2-5 column volumes of equilibration buffer 1 followed by 5 column volumes of equilibration 2. The column was then loaded to 55 mg product/ml resin with the Protein A peak (adjusted to the appropriate equilibration 2 buffer), and the product was recovered in the column effluent during the load cycle and some column volumes of the wash fraction. The results from these experiments are presented in Table 7.2.1 and FIG. 13.

TABLE 7.2.1

Partition coefficients for MAB-MYO on cHA resin and the corresponding operating mode

| | Partition Coefficient Kp | Operating mode | Arg mM | Hepes mM | Phos mM | NaCl mM | Product Bound mg/ml |
|---|---|---|---|---|---|---|---|
| Run 1 | 3.6 | Weak Partitioning | 50 | 20 | 8 | 300 | 5.1 |
| Run 2 | 4.2 | Weak Partitioning | 50 | 20 | 2 | 600 | 8.2 |
| Run 3 | 8.9* | Weak Partitioning | 12 | 20 | 1 | 1750 | 9.5 |
| Run 4 | >100 | Strong Binding | 50 | 50 | 5 | 50 | 41.6 |

Figure 13:
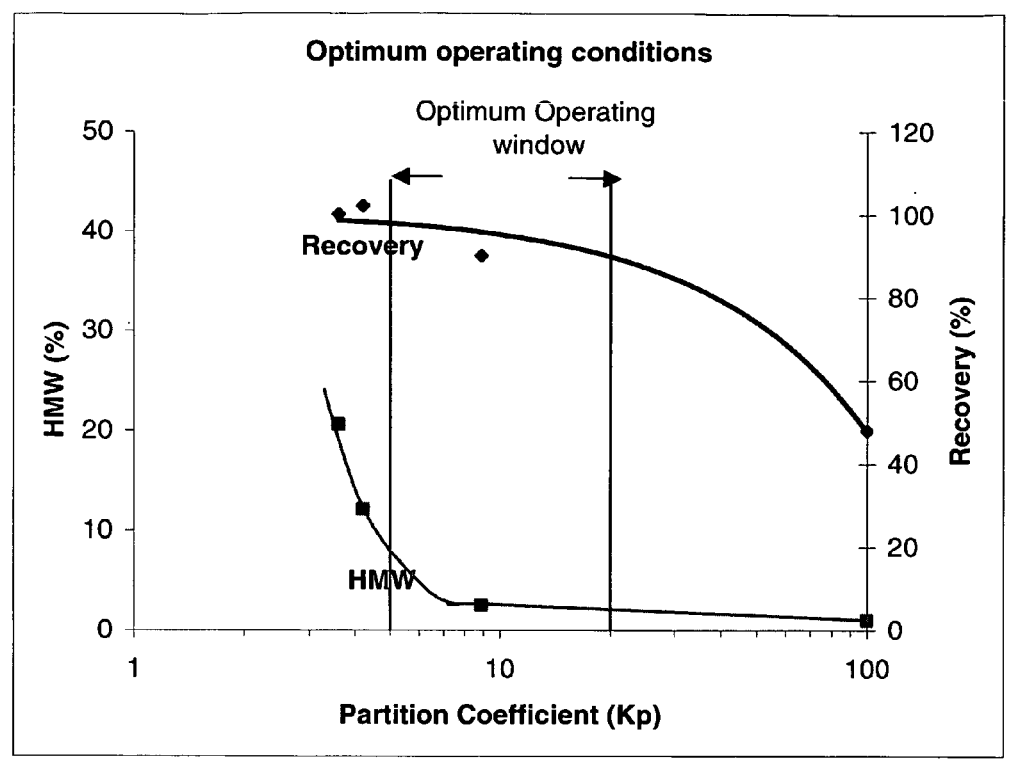
FIG. 13 shows for Mab-MYO, the optimum operating window for weak partitioning chromatography in hydroxyapatite. The optimum Kp in this example is between 5 and 20.

*Optimal Kp condition, see FIG. 13

The operating conditions in these experiments correspond to the flow-through, weak partitioning (WP) and binding regions. The HTS experiment described in Experiment 7.1 provides estimates for the value of the partition coefficient (Kp) under these conditions of pH, chloride, phosphate, glycine/arginine and HEPES concentration. The runs in Table 7.2.1 are ranked by the partition coefficients. The bound product was determined by measuring the protein in the column strip using UV absorbance. This method of determining the bound product typically underestimates the amount of product bound during the load due to the gradual desorption of the product during the wash. The product related High Molecular weight (HMW) removal and product recovery results from these experiments are also presented in FIG. 13. It is evident from the data presented in FIG. 13 that the performance of the cHA step improves significantly with respect to HMW reduction as we move from flow-through conditions to weak partitioning conditions, while product recovery is >80%. Operating under conditions corresponding to a further increase in the partition coefficient (i.e., operating in the binding region) provides no additional benefit with respect to contaminant removal. However, the product recovery across the step begins to drop under strong binding conditions. Thus, the optimum operating window for this separation corresponds to that of weak partitioning chromatography. Under these conditions, a 20-fold reduction of product related HMW species was obtained. The bound product levels under the weak partitioning conditions, in this example, were between 5.1-9.5 mg/ml of the resin.

Summary

A second example was presented in hydroxyapatite where operating under weak partitioning chromatography was shown to provide improved performance with respect to HMW reduction with good product recovery (>80%). Product related HMW species and HMW species bind more tightly to ceramic resin than the product antibody, and is retained strongly under WP conditions. The WP region in this example corresponds to partition coefficients between 8 and 20.

It was once again shown that the performance of the column step can be optimized primarily through the choice of partition coefficients used to run the column. The approach presented here provides a simple means of relating the impact of changing any one of several variables (pH, salt, phosphate, arginine, HEPES etc.,) to column performance. The weak partitioning conditions for optimum performance can easily be identified using the HTS methods described in this example. The approach presented here opens up the possibility of operating in a wider operating space in this mode of chromatography than has been done before.

It is also worth noting here that the concept of weak partitioning chromatography also works in systems that are not driven by charge interactions alone. The general approach described in this application can be successfully applied to complex systems such as HIC and hydroxyapatite as well. For example, in addition to the operating pH, several other variables such as NaCl, phosphate salts, arginine/glycine, buffering species, as well as the type of resin can all impact step performance in hydroxyapatite. Nevertheless, one could easily identify the WP window by performing simple batch binding experiments with the product of interest alone.

Series 8—Zwitterionic Buffer for Protein A Elution and Subsequent Ion Exchange Steps A culture containing a monoclonal antibody was purified using MabSelect resin. A Mabselect Protein A column was equilibrated with 5 column volumes of 50 mM Tris/150 mM NaCl, pH 7.5. The column was then loaded at a load of approximately 40 mg product/ml resin. This was followed by a 5CV wash in 1M NaCl, 50 mM Tris, pH 7.5 and a 5CV wash containing 10 mM Tris, 75 mM NaCl, pH 7.5 wash. The column was then eluted using 30 mM HEPES, pH 3.1. The product pool was neutralized to pH 7.2 using 1M HEPES pH 8.0, resulting in a total HEPES concentration of 55 mM. At pH 7.2, the HEPES contributes 17 mM ionic strength to the buffer.

All references cited herein are incorporated herein by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supercede and/or take precedence over any such contradictory material.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

We claim:

1. A method of recovering a purified product from a load fluid, comprising the steps of:
   passing the load fluid through a medium to obtain a column effluent, at operating conditions which cause the medium to bind at least about 2.8 mg of product per mL of medium, wherein the medium is selected from the group consisting of a charged ion exchange medium, a hydrophobic interaction chromatography resin, and an immobilized metal affinity chromatography resin; and
   recovering the purified product in the column effluent.

2. A method of recovering a purified product from a load fluid, comprising the steps of:
   passing the load fluid through a medium to obtain a column effluent, at operating conditions defined by a partition coefficient of at least about 0.1; and
   recovering the purified product in the column effluent.

3. A method of recovering a purified product from a load fluid, comprising the steps of:
   passing the load fluid through a medium to obtain a column effluent, at operating conditions which cause the medium to bind about 2.8 to about 13 mg of product per mL of medium; and
   recovering the purified product in the column effluent.

4. A method of recovering a purified product from a load fluid, comprising the steps of:
   passing the load fluid through a medium at operating conditions which cause the medium to bind at least about 1 mg of product per mL of medium, wherein the medium is selected from the group consisting of a hydrophobic interaction chromatography resin and an immobilized metal affinity chromatography resin; and
   recovering the purified product from column effluent.

5. A method of recovering a purified antibody from a load fluid, comprising the steps of:
   passing the load fluid through a charged anion exchange medium to obtain a column effluent, at operating conditions which cause the medium to bind at least about 2.8 mg of antibody per mL of medium, wherein the operating conditions comprise a pH of about 7.5 to about 8.2 and a chloride concentration of about 12 to about 55 mM, and wherein the load fluid is a product-containing fluid eluted from a Protein A column; and
   recovering the purified antibody in the column effluent.

6. A method of recovering a purified antibody from a load fluid, comprising the steps of:
   passing the load fluid through a charged anion exchange medium to obtain a column effluent, at operating conditions defined by a partition coefficient of at least about 1.0; wherein the operating conditions comprise a pH of about 7.5 to about 8.2 and a chloride concentration of about 12 to about 55 mM, and wherein the load fluid is a product-containing fluid eluted from a Protein A column; and recovering the purified antibody in the column effluent during the load cycle and any essentially isocratic wash.

7. A method of recovering a purified product from a load fluid, comprising the steps of:
passing the load fluid through a medium to obtain a column effluent, at operating conditions which cause the medium to bind at least about 1 mg of product per mL of medium; and
recovering at least about 98% of the product in the column effluent.

8. A method of recovering a purified product from a load fluid, comprising the steps of:
passing the load fluid through a medium to obtain a column effluent, at operating conditions which cause the medium to bind at least about 3.0 mg of product per mL of medium; and
recovering at least about 93% of the product in the column effluent.

9. The method of claim 1, wherein the operating conditions cause the medium to bind at least about 10 mg of product per mL of medium.

10. The method of claim 2, wherein the value of the partition coefficient is in the range of about 0.2 to about 10.0.

11. The method of any one of claims 1-3 and 6-8, further comprising the step of recovering the purified product from the medium using an essentially isocratic wash.

12. The method of any one of claims 1-3 and 5-8, wherein the purified product is a protein selected from the group consisting of fusion proteins, Fc-containing proteins, immunoconjugates, cytokines, interleukins, hormones, and therapeutic enzymes.

13. The method of any one of claims 1, 2, 3, 7 and 8, wherein the operating conditions comprise a pH of about 7.5 to about 8.2 and a chloride concentration of about 12 to about 55 mM.

14. The method of any one of claims 1-3 and 5-8, wherein the load fluid further comprises at least one of phosphate, calcium, arginine, glycine, HEPES, and counterligand.

15. The method of claim 14, wherein the counterligand is imidazole.

16. The method of claim 1, wherein the operating conditions cause the medium to bind at least about 8 mg of product per mL of medium.

17. The method of claim 16, wherein the operating conditions cause the medium to bind at least about 14 mg of product per mL of medium.

18. The method of claim 1, wherein the operating conditions cause the medium to bind about 2.8 to about 12 mg of product per mL of medium.

19. The method of claim 18, wherein the operating conditions cause the medium to bind about 2.8 to about 5 mg of product per mL of medium.

20. The method of claim 18, wherein the operating conditions cause the medium to bind about 8 to about 12 mg of product per mL of medium.

21. The method of claim 2, wherein the value of the partition coefficient is in the range of about 0.5 to about 15.

22. The method of claim 21, wherein the value of the partition coefficient is in the range of about 0.5 to about 2.5.

23. The method of claim 12, wherein the Fc-containing protein is an antibody.

24. The method of claim 2, wherein the medium comprises a charged ion exchange medium.

25. The method of claim 1 or 24, wherein the charged ion exchange medium comprises an anion exchange resin.

26. The method of claim 1 or 24, wherein the charged ion exchange medium comprises a cation exchange resin.

27. The method of claim 2, wherein the medium comprises a hydrophobic interaction chromatography resin.

28. The method of claim 2, wherein the medium comprises a hydroxyapatite resin.

29. The method of claim 2, wherein the medium comprises an immobilized metal affinity chromatography resin.

30. The method of any one of claims 1-3 and 5-8, wherein the load fluid comprises one or more impurities selected from the group consisting of host cell proteins, nucleic acids, product variants, endotoxins, Protein A, and viruses, or any combinations thereof.

31. The method of any one of claims 1-3 and 5-8, wherein the load fluid is a product-containing fluid eluted from a Protein A column using an elution buffer and the pH and conductivity of the product-containing fluid is adjusted using a neutralization buffer which results in no more than about 20 mM of the ionic strength of the product-containing fluid.

32. The method of claim 31, wherein the elution buffer comprises molecules with a charged anionic group with a pKa of about 2 to about 5.

33. The method of claim 31, wherein the elution buffer further comprises molecules with a charged cationic group with a pKa of about 6.5 to about 10.

34. The method of claim 31, wherein the elution buffer comprises a molecule that is a zwitterion at a pH of about 4 to about 9.

35. The method of claim 34, wherein the zwitterion is selected from the group consisting of glycine; 1,4-piperazinebis-(ethanesulfonic acid); glycylglycine; cyclopentanetetra-1,2,3,4-carboxylic acid; N,N-bis(2-hydroxyethyl)-2-aminoethanesulfonicacid; 2-(N-morpholino)propanesulfonic acid; N-tris (hydroxymethyl)methyl-2-aminoethane sulfonic acid; N-2-hydroxyethylpiperazine-N'-2-ethanesulfonicacid; 4-(2-hydroxyethyl)-l-piperazinepropane sulfonic acid; N-tris (hydroxymethyl)methylglycine; glycinamide; N,N-bis(2-hydroxyethyl)glycine; N-tris (hydroxymethyl)methyl-2-aminopropane sulfonic acid; and N-glycylglycine.

36. The method of claim 35, wherein the zwitterion is glycine.

37. The method of any one of claims 1-3 and 5-8, wherein the product is loaded onto the medium at a concentration of least about 100 mg of product per mL of medium.

38. The method of claim 37, wherein the product is loaded onto the medium at a concentration of least about 500 mg of product per mL of medium.

39. The method of claim 38, wherein the product is loaded onto the medium at a concentration of least about 1000 mg of product per mL of medium.

40. The method of any one of claims 1-3 and 5-8, wherein the concentration of product in the load fluid is at least about 1 mg of product per mL of load fluid.

41. The method of claim 40, wherein the concentration of product in the load fluid is at least about 10 mg of product per mL of load fluid.

42. The method of claim 41, wherein the concentration of product in the load fluid is at least about 100 mg of product per mL of load fluid.

43. The method of any one of claims 1-3 and 5-6, wherein at least about 89% of the product is recovered in the column effluent.

44. The method of claim 43, wherein at least about 95% of the product is recovered in the column effluent.

* * * * *

UNITED STATES PATENT AND TRADEMARK OFFICE
CERTIFICATE OF CORRECTION

| | | |
|---|---|---|
| PATENT NO. | : 8,067,182 B2 | Page 1 of 1 |
| APPLICATION NO. | : 11/372054 | |
| DATED | : November 29, 2011 | |
| INVENTOR(S) | : Kelley et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 790 days.

Signed and Sealed this
Tenth Day of April, 2012

David J. Kappos
*Director of the United States Patent and Trademark Office*